(12) United States Patent
Kono et al.

(10) Patent No.: US 11,098,078 B2
(45) Date of Patent: Aug. 24, 2021

(54) PEPTIDE SYNTHESIS METHOD

(71) Applicant: JITSUBO Co., Ltd., Kanagawa (JP)

(72) Inventors: Yusuke Kono, Kanagawa (JP); Hideaki Suzuki, Kanagawa (JP); Susumu Muto, Kanagawa (JP)

(73) Assignee: JITSUBO Co., Ltd., Kanagawa (JP)

( * ) Notice: Subject to any disclaimer, the term of this patent is extended or adjusted under 35 U.S.C. 154(b) by 907 days.

(21) Appl. No.: 15/555,484

(22) PCT Filed: Mar. 2, 2016

(86) PCT No.: PCT/JP2016/056319
§ 371 (c)(1),
(2) Date: Jan. 5, 2018

(87) PCT Pub. No.: WO2016/140232
PCT Pub. Date: Sep. 9, 2016

(65) Prior Publication Data
US 2018/0215782 A1 Aug. 2, 2018

(30) Foreign Application Priority Data
Mar. 4, 2015 (JP) .............................. JP2015-042651

(51) Int. Cl.
| C07K 1/00 | (2006.01) |
|---|---|
| C07K 1/02 | (2006.01) |
| C07K 1/10 | (2006.01) |
| C07C 43/23 | (2006.01) |
| C07C 43/225 | (2006.01) |
| C07C 217/58 | (2006.01) |
| C07K 1/30 | (2006.01) |

(52) U.S. Cl.
CPC ............ *C07K 1/026* (2013.01); *C07C 43/225* (2013.01); *C07C 43/23* (2013.01); *C07C 217/58* (2013.01); *C07K 1/10* (2013.01); *C07K 1/306* (2013.01)

(58) Field of Classification Search
CPC ..... C07C 217/58; C07C 43/225; C07C 43/23; C07K 1/026; C07K 1/10; C07K 1/306
See application file for complete search history.

(56) References Cited

U.S. PATENT DOCUMENTS

| 5,516,891 | A | 5/1996 | Siwruk et al. |
|---|---|---|---|
| 2003/0018164 | A1 | 1/2003 | Eggen et al. |
| 2004/0214989 | A1 | 10/2004 | Chiba et al. |
| 2009/0069538 | A1 | 3/2009 | Murao et al. |
| 2009/0299103 | A1 | 12/2009 | Chiba et al. |
| 2010/0029904 | A1 | 2/2010 | Chiba et al. |
| 2010/0240867 | A1 | 9/2010 | Takahashi |
| 2010/0249374 | A1 | 9/2010 | Takahashi |
| 2014/0088291 | A1* | 3/2014 | Takahashi ............... C07K 1/061 530/335 |
| 2014/0214989 | A1 | 7/2014 | Heikes et al. |

FOREIGN PATENT DOCUMENTS

| EP | 2716650 A1 | 4/2014 | |
|---|---|---|---|
| EP | 2716650 | 9/2014 | |
| JP | H06509821 A | 11/1994 | |
| JP | 2003500415 A * | 1/2003 | ............... C07K 1/02 |
| JP | 2003500415 A | 1/2003 | |
| JP | 200355396 A1 | 2/2003 | |
| JP | 2003183298 A | 7/2003 | |
| JP | 2004059509 A | 2/2004 | |
| WO | 200071569 A1 | 11/2000 | |
| WO | 2006104166 A1 | 10/2006 | |
| WO | 2007122847 A1 | 1/2007 | |
| WO | 2007034812 A1 | 3/2007 | |
| WO | 2007099656 A1 | 9/2007 | |
| WO | WO-2007099656 A1 * | 9/2007 | ......... C07K 5/06078 |
| WO | 2010104169 A1 | 9/2010 | |
| WO | 2010113939 A1 | 10/2010 | |

OTHER PUBLICATIONS

English language translation of JP2003/500415 from Google patents accessed Dec. 7, 2020 (Year: 2003).*
English language translation of WO 2007/099656 from Google patents accessed Dec. 7, 2020 (Year: 2007).*
Extended European Search Report dated Apr. 9, 2018 for European National Phase application No. 16758925.8.
European Office Action for European Patent Application No. 16 758 925.8 dated Jan. 29, 2020.
Daisuke Takahashi et al: "Novel diphenylmethyl-Derived Amide Protecting Group for Efficient Liquid-Phase Peptide Synthesis: AJIPHASE", Organic Letters, vol. 14, No. 17, Sep. 7, 2012 (Sep. 7, 2012), pp. 4514-4517, XP55246787, ISSN: 1523-7060, DOI: 10.1021/ol302002g.

(Continued)

*Primary Examiner* — James H Alstrum-Acevedo
*Assistant Examiner* — Mercy H Sabila
(74) *Attorney, Agent, or Firm* — Hunton Andrews Kurth LLP

(57) ABSTRACT

The present invention has an object of providing a peptide synthesis method using a carrier capable of reversibly repeating the dissolved state and the insolubilized state, wherein the problem of an amino acid active species existing in the reaction system in de-protection reaction can be easily solved. The present invention provides a peptide synthesis method comprising the following steps: a step of condensing an N-Fmoc protected amino acid with a peptide having a C-terminal protected with a carrier which is crystallized according to a change of a composition of a dissolving solvent, in the presence of a condensing agent, to obtain an N-Fmoc-C-carrier protected peptide, a step of adding an alkylamine having 1 to 14 carbon atoms or hydroxyl amine to the reaction system, a step of de-protecting the N-terminal, and a step of changing the composition of the solvent dissolving the C-carrier protected peptide, to crystallize and separate the peptide.

21 Claims, No Drawings
Specification includes a Sequence Listing.

(56) References Cited

OTHER PUBLICATIONS

Daisuke Takahashi et al: "Development of an efficient liquid-phase peptide synthesis protocol using a novel fluorene-derived anchor support compound with Fmoc chemistry; AJIPHASE", Tetrahedron Letters, Elsevier Ltd, Amsterdam, NL, vol. 53, No. 15, Feb. 2, 2012 (Feb. 2, 2012), pp. 1936-1939, XP028466059, ISSN: 0040-4039, DOI: 10.1016/J.TETLET.2012.02.006 [retrieved on Feb. 9, 2020].
Daisuke Takahashi et al: "Supplementary Data Development of an efficient liquid-phase peptide synthesis protocol using a novel fluorine-derived anchor support compound with Fmoc chemistry; AJIPHASE", tetrahedron letters, vol. 53, Feb. 9, 2012 (Feb. 9, 2012), pp. s1-s5, XP055661328.
Sheppeck II, James, et aL., "A convenient and scaleable procedure for removing the Fmoc group in solution", Tetrahedorn Letters 41 (2000), 5329-5333.
Carpino, A.L., et, al., "Rapid, Continuous Solution-Phase Peptide Synthesis: Application to Peptides of Pharmaceutical Interest", Org. Process Res. Dev., 2003, vol. 7, issue 1, p. 28-37.
Eggen, Ivo F., et, al., "A novel method for repetitive peptide synthesis in solution without isolation of intermediates", J. Pept. Sci., 2005, vol. 11, issue 10, p. 633-641.
International Search Report and Written Opinion for PCT/JP2016/056319 dated May 31, 2016.

* cited by examiner

PEPTIDE SYNTHESIS METHOD

CROSS REFERENCE TO RELATED APPLICATIONS

This application is a National Stage application from PCT/JP2016/056319 filed Mar. 2, 2016, which claims Priority to Japanese Patent application 2015-042651 filed Mar. 4, 2015.

FIELD OF THE INVENTION

The present invention relates to a novel peptide synthesis method, specifically, to a peptide synthesis method capable of easily performing a accurate peptide elongation reaction.

BACKGROUND OF THE INVENTION

Conventionally, methods in which specific components dissolved in a liquid are separated as a solid, in a chemical process, are widely used. The reason for this is that separation and purification after the reaction become easy by solidifying (crystallizing) only specific components. According to this method, for example, a necessary or unnecessary compound is solidified (crystallized) after completion of each reaction in sequential multi-step synthesis such as synthesis of a compound library and the like used in recent developments and studies of pharmaceutical preparations, resultantly, the solidified (crystallized) substance can be easily separated and purified. Thus, process complexity as the conventional problem can be solved.

There is also used a method in which a specific component dissolved is selectively dissolved in a specific phase (selective distribution) in liquid phase separation, to realize separation from other components. This method can contribute to rapid and simplified processes, since a specific component can be separated without solidification (crystallization).

Solidification (crystallization) of a specific component dissolved in a solution or selective dissolution of a specific component into a specific liquid phase (selective distribution) as described above is realized by satisfying certain conditions regarding chemical natures of a compound, physical properties thereof and the solvent. However, conditions of solidification (crystallization) and selective dissolution (selective distribution) should be empirically searched via trial and error in many cases. Particularly in sequential multi-step synthesis, significant cost and time are necessary for process development, since it is necessary to investigate conditions of respective steps based on natures specific to compounds synthesized in respective steps.

Then, a carrier molecule having a linker, which sensitively detects a change of the solvent composition thereby causing a reversible change between the dissolved state and the insolubilized (crystallized) state or causes selective dissolution of a specific component dissolved into a specific phase at high concentration (selective distribution) in liquid phase separation, is suggested. Various compounds can be bonded to such a carrier molecule via a linker. Thus, the bonded compounds can easily undergo a state variation from the dissolved state to the insolubilized (crystallized) state or inversely, together with the carrier molecule. Alternatively, the compounds bonded to the carrier molecule can be dissolved at high concentration selectively (selective distribution) into a specific phase of a liquid separated into several phases.

Further, such a carrier molecule can reversibly repeat the dissolved state and the insolubilized (crystallized) state under approximately the same condition even if the chemical structure of the bonded compound varies by the sequential chemical reaction, or can cause selective dissolution at high concentration (selective distribution) into a specific phase of a liquid separated in several phases. When a carrier molecule which causes a reversible change between the dissolved state and the insolubilized (crystallized) state or can induce the selective distribution state as described above is used, a compound as the separation target can be selectively separated from the uniform dissolved state, using knowledge of general liquid phase reactions in organic chemistry as it is. That is, a specific compound can be separated while leaving other soluble components in the solution after the liquid phase reaction.

As the carrier capable of reversibly repeating the dissolved state and the insolubilized state, various compounds are suggested. For example, a benzyl alcohol compound to which a long chain fatty acid is introduced suggested by the present inventors (Patent documents 1 to 4), or a fluorene compound to which a long chain fatty acid is introduced (Patent document 5) and a diphenylmethane compound to which a long chain fatty acid is introduced (Patent document 6) are listed.

The peptide synthesis technology includes a solid phase peptide synthesis method (SPPS method) and a liquid phase peptide synthesis method (LPPS method). In the solid phase peptide synthesis method, purification cannot be conducted at each step of the amino acid elongation reaction, in principle. Since the synthesis cost is high, this method is suitable for small volume production. In contrast, the liquid phase peptide synthesis method is widely used for large scale production, however, when the length of the peptide chain increases, the peptide elongation reaction becomes difficult, thus, synthesis of a long chain peptide is problematic.

For this reason, it is suggested to conduct peptide synthesis using the above-described carrier capable of reversibly repeating the dissolved state and the insolubilized state (Patent documents 1 to 6).

Peptide synthesis has a problem of deletion of an amino acid residue occurring in the peptide elongation reaction, and it is problematic also in the case of use of the above-described carrier. For solving deletion of an amino acid residue, equivalents of an amino acid and a condensing agent are increased. However, when an excessive amino acid active species remains in the reaction liquid as its result, there is a new problem that double hit occurs in de-protection of an N-terminal. By this, the yield of the intended amino acid lowers. The double hit denotes that one extra amino acid residue is further inserted into the target peptide.

As the solution means for this, an amino acid active species is removed from the reaction system by washing before de-protection. For example, a method as described below is suggested. There is a suggestion on a method of adding an amine having an anion component such as β-alanine-OBz or the like as a scavenger, for removing an active ester of an amino acid remaining in the reaction system in a liquid phase peptide synthesis method using a benzyloxycarbonyl group (Cbz or Z) or a t-butyloxycarbonyl group (Boc) as a protective group (Patent document 7). In this method, also an anion component protective group of a scavenged body is eliminated simultaneously in de-protecting a protective group from an N-terminal, resulting in the scavenged body becoming water-soluble. Thereafter, liquid-liquid extraction is conducted using an alkaline water-organic solvent, then, a condensing agent and an amino acid component are removed by water. However, when Cbz is used as a protective group, the de-protection catalyst is deactivated if Met or Cys is present on the peptide sequence, that is, this is not applicable. Further, in this method, fluorenylmethoxycarbonyl (Fmoc) cannot be used as a protective group, since dibenzofulvene cannot be removed.

Further, there is a suggestion on a method of removing an amino acid component by liquid-liquid extraction while hydrolyzing an active ester with alkali water (for example, a 5% sodium carbonate aqueous solution), for removing an active ester of an amino acid remaining in the reaction system in a liquid phase peptide synthesis method using Boc as a protective group (Patent document 8). In this method, however, epimerization possibly occurs under strong alkali condition of pH=11 or more. Additionally, fluorenylmethoxycarbonyl (Fmoc) cannot be used as a protective group, since dibenzofulvene cannot be removed.

Also in peptide synthesis using a carrier capable of reversibly repeating the dissolved state and the insolubilized state described above, an amino acid active species can be removed from the reaction system by washing before de-protection for solving the problem of double hit due to an excessive amino acid active species. However, an amino acid active species cannot be removed completely by washing in some cases by a crystallization operation for insolubilizing the carrier, and there is a problem that twice washing operations after the condensation reaction and after de-protection are required and a large amount of a washing solvent is necessary.

Further, there is a report on a method in which Fmoc is de-protected from an N-terminal, then, thiolcarboxylic acid is allowed to coexist and dibenzofulvene is generated, then, liquid-liquid extraction is performed with an alkaline water-organic solvent, then, a condensing agent, an amino acid component and dibenzofulvene are removed by water, thereby removing an amino acid active ester, as the method of removing a Fmoc group in peptide synthesis (Patent document 8). Further, it is disclosed that an active ester may be removed by thiol silica or decomposed with alkali water before de-protection of Fmoc and it is suggested that an active ester of an amino acid is removed in the form of a water-soluble product.

In addition, there is a report on a method in which Fmoc is de-protected from an N-terminal, then, alkyl thiol or solid phase thiol is allowed to coexist and dibenzofulvene is generated, then, condensation is performed, then, a peptide component is crystallized with an ether and solid-liquid separation is conducted, to remove dibenzofulvene adduct, as the method of removing a Fmoc group in peptide synthesis, however, removal of an amino acid active ester is not described (Non-Patent document 1).

CITATION LIST

Patent Literature

Patent Literature 1: Japanese Unexamined Patent Application Publication No. 2003-183298
Patent Literature 2: Japanese Unexamined Patent Application Publication No. 2004-059509
Patent Literature 3: WO 2007/034812
Patent Literature 4: WO 2007/122847
Patent Literature 5: WO 2010/104169
Patent Literature 6: WO 2010/113939
Patent Literature 7: Japanese Unexamined Patent Application Publication No. 2003-55396
Patent Literature 8: WO 2007/099656

Non-Patent Literature

Non-Patent Literature 1: James E. Sheppeck II et al., Tetrahedorn Letters 41 (2000)

SUMMARY OF THE INVENTION

Technical Problem

The present invention has an object of providing a peptide synthesis method using a carrier capable of reversibly repeating the dissolved state and the insolubilized state, wherein the problem of an amino acid active species existing in the reaction system in de-protection reaction can be easily solved.

Solution to Problem

The present inventors have intensively studied in consideration of the above-described problem and resultantly found that double hit of an amino acid can be prevented in de-protection by deactivating an amino acid active species by a specific scavenger before the de-protection reaction, even if the amino acid active species is not removed from the reaction system before de-protection of an N-terminal, leading to completion of the present invention. The present invention includes the followings.

(1) A peptide synthesis method comprising the following steps a to d:
   a. a step of condensing an amino acid having an N-terminal protected with fluorenylmethoxycarbonyl (N-Fmoc protected) or an N-Fmoc protected peptide with an amino acid having a C-terminal protected with a carrier which is crystallized according to a change of a composition of a dissolving solvent (C-carrier protected), a C-carrier protected peptide or a C-carrier protected amino acid amide, in the presence of a condensing agent, to obtain an N-Fmoc-C-carrier protected peptide,
   b. a step of adding at least one amine selected from the group consisting of an alkylamine having 1 to 14 carbon atoms, an aromatic amine having 1 to 14 carbon atoms and hydroxyl amine to a reaction system, wherein the alkylamine or the aromatic amine is a primary or secondary amine),
   c. a step of de-protecting the N-terminal, and
   d. a step of changing a composition of a solvent dissolving the resultant C-carrier protected peptide, to crystallize and separate the C-carrier protected peptide.

(2) The peptide synthesis method according to the above (1), wherein said carrier is a compound selected from the group consisting of
a compound having the following structure (in the present specification, referred to as "Ka" in some cases):

[Chemical Formula 1]

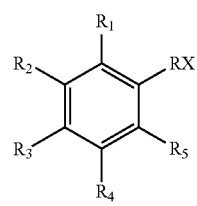

(wherein, $R_1$ and $R_5$ represent a hydrogen atom, and $R_2$, $R_3$ and $R_4$ represent an alkoxyl group having 8 to 30 carbon atoms, preferably an alkoxyl group having 11 to 22 carbon atoms. In the formula, RX is a group represented by the following formula and binding to the C-terminal of a peptide or an amino acid,

[Chemical Formula 2]

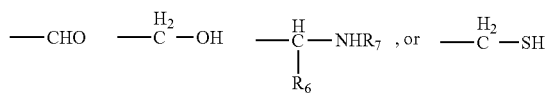

(wherein, $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group. The above-described formula is shown in the state before binding to the C-terminal of a peptide or an amino acid.), a compound having the following structure (in the present specification, referred to as "Kb" in some cases):

[Chemical Formula 3]

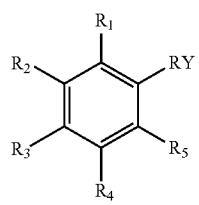

(wherein, $R_2$, $R_4$ and $R_5$ represent a hydrogen atom, and $R_1$ and $R_3$ represent an alkoxyl group having 12 to 30 carbon atoms, preferably an alkoxyl group having 18 to 22 carbon atoms. In the formula, RY is a group represented by the following formula and binding to the C-terminal of a peptide or an amino acid,

[Chemical Formula 4]

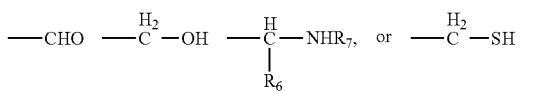

(wherein, $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group. The above-described formula is shown in the state before binding to the C-terminal of a peptide or an amino acid.), and a compound having the following structure (in the present specification, referred to as "Kc" in some cases):

[Chemical Formula 5]

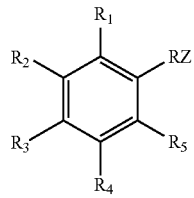

(wherein, $R_1$, $R_3$ and $R_5$ represent a hydrogen atom, and $R_2$ and $R_4$ represent an alkoxyl group having 12 to 30 carbon atoms, preferably an alkoxyl group having 18 to 22 carbon atoms. In the formula, RZ is a group represented by the following formula and binding to the C-terminal of a peptide or an amino acid,

[Chemical Formula 6]

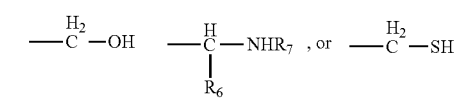

(wherein, $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group. The above-described formula is shown in the state before binding to the C-terminal of a peptide or an amino acid.).

(3) The peptide synthesis method according to the above (1), wherein said carrier is a compound selected from the group consisting of

[Chemical Formula 7]

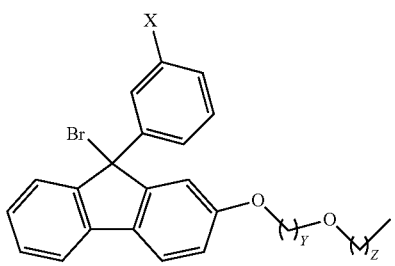

(wherein, X represents a halogen, Y is an integer of 8 to 12 and Z is an integer of 17 to 29.),

[Chemical Formula 8]

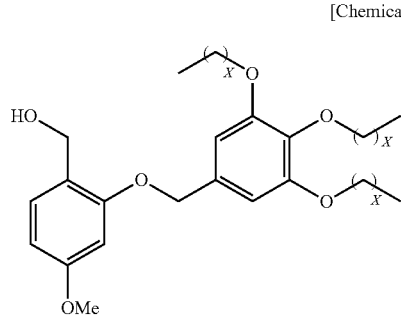

(wherein, marks X each independently represent an integer of 7 to 21.) and

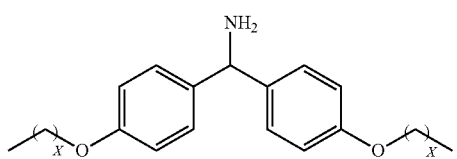

[Chemical Formula 9]

(wherein, marks X each independently represent an integer of 11 to 29.)

(The above-described formulae are shown in the state before binding to the C-terminal of a peptide or an amino acid.).

(4) The peptide synthesis method according to the above (1), wherein said carrier is a compound selected from the group consisting of

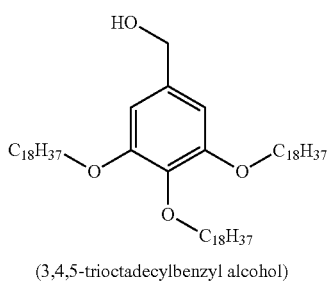

[Chemical Formula 10]

(3,4,5-trioctadecylbenzyl alcohol)

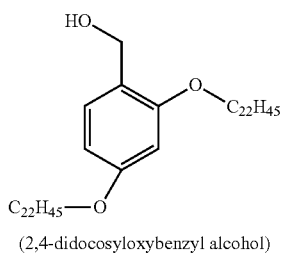

[Chemical Formula 11]

(2,4-didocosyloxybenzyl alcohol)

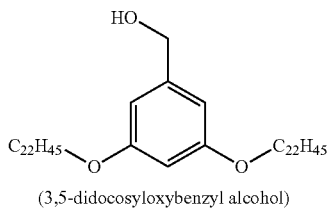

[Chemical Formula 12]

(3,5-didocosyloxybenzyl alcohol)

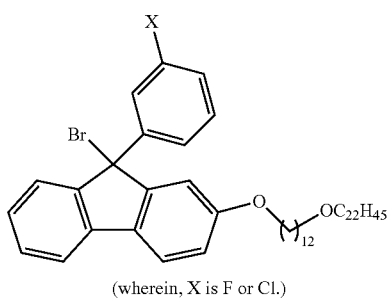

[Chemical Formula 13]

(wherein, X is F or Cl.)

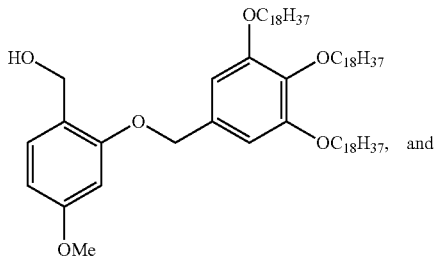

[Chemical Formula 14]

((2-(3,4,5-trioctadecyloxybenzyl)-4-methoxybenzyl alcohol)

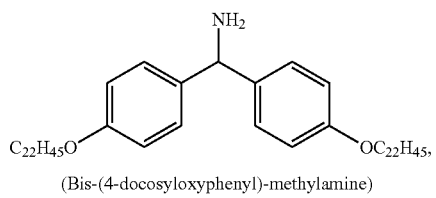

[Chemical Formula 15]

(Bis-(4-docosyloxyphenyl)-methylamine)

(The above-described formulae are shown in the state before binding to the C-terminal of a peptide or an amino acid.).

(5) The peptide synthesis method according to any one of the above (1) to (4), wherein said amine is an alkylamine having 1 to 10 carbon atoms or hydroxylamine.

(6) The peptide synthesis method according to any one of the above (1) t0 (5), wherein said amine is an alkylamine having 3 or 4 carbon atoms.

(7) The peptide synthesis method according to any one of the above (1 to (6), wherein the amine equivalent in the step b is 1 to 30-fold amount with respect to the amino acid equivalent theoretically remaining after the condensation reaction of the step a.

(8) The peptide synthesis method according to any one of the above (1) to (7), wherein the composition changing means for changing the composition of the solvent dissolving the resultant C-carrier protected peptide is performed by concentrating the solvent of the solution, then, adding a poor solvent to attain solidification.

(9) The peptide synthesis method according to the above (8), wherein said poor solvent is a solvent selected from the group consisting of acetonitrile, aqueous acetonitrile, methanol, aqueous methanol and water.

(10) The peptide synthesis method according to any one of the above (1) to (9), comprising conducting repetition of the step a to the step d using the C-carrier protected peptide crystallized and separated in the step d.

(11) The peptide synthesis method according to any one of the above (1) to (10), further comprising the following step:

e. a step of washing the crystal of the C-carrier protected peptide crystallized and separated with an organic solvent.

(12) The peptide synthesis method according to any one of the above (1) to (11), wherein said steps a to c are conducted in one pot synthesis.

Advantageous Effect of Invention

The peptide synthesis method of the present invention can solve the problem of an amino acid active species existing in the reaction system in the de-protection reaction by a simple means and is excellent in versatility. The peptide synthesized by the present invention has less problems of deletion of an amino acid and double hit, thus, according to the method of the present invention, a peptide of high quality can be synthesized at high yield.

DESCRIPTION OF EMBODIMENTS

Hereinafter, the present invention will be illustrated and described in detail with reference to the exemplary embodiments, along with the preferred methods and materials which can be used in practice of the present invention.

Unless otherwise specified in the sentences, any technical terms and scientific terms used in the present specification, have the same meaning as those generally understood by those of ordinary skill in the art to which the present invention belongs. Any materials and methods equivalent or similar to those described in the present specification can be used for practicing the present invention.

All publications and patents cited herein in connection with the present invention described herein are incorporated herein by reference, for example, as indicating methodology, materials, etc. that can be used in the present invention.

Terms used in the present specification will be explained below.

1. N-Fmoc protected amino acid and peptide

The amino acid having an N-terminal protected by fluorenylmethoxycarbonyl (Fmoc) (N-Fmoc protected amino acid) denotes an amino acid in which an amino group of the amino acid is protected by Fmoc, while a carbonyl group is not protected and is reactive.

The peptide having an N-terminal protected by fluorenylmethoxycarbonyl (Fmoc) (N-Fmoc protected peptide) denotes a peptide in which an amino group at the N-terminal of the peptide chain is protected by Fmoc, while, a carbonyl group at the C-terminal is not protected and is reactive.

When the N-Fmoc protected amino acid or the N-Fmoc protected peptide has a functional group rich in reactivity such as a hydroxyl group, an amino group, a guanidyl group, a carboxyl group, a sulfhydryl group and the like, a general protective group used in peptide chemistry may be introduced into these functional groups, and after completion of the reaction, the protective group is removed if necessary, thus, the target compound can be obtained.

The protective group for a hydroxyl group includes a tBu group, a Trt group, a Bz group, an acetyl group, a silyl group and the like, the protective group for an amino group includes a Boc group, a Fmoc group, a Cbz group, a Trt group, an Mmt group, an ivDde group and the like, the protective group for a guanidyl group includes a Pbf group, a Pmc group, a nitro group and the like, the protective group for a carboxyl group includes a tBu group, a methyl group, an ethyl group, a Bz group and the like, and the protective group for a sulfhydryl group includes a Trt group, an Acm group, a tBu group, an S-tBu group and the like.

2. C-Carrier Protected Amino Acid, Peptide and Amino Acid Amide

The amino acid having a C-terminal protected by a carrier which is crystallized according to a change of a composition of a dissolving solvent (C-carrier protected amino acid) denotes an amino acid in which a carboxyl group of the amino acid is protected by a carrier described later, while an amino group is not protected and is reactive.

The peptide having a C-terminal protected by a carrier which is crystallized according to a change of a composition of a dissolving solvent (C-carrier protected peptide) denotes a peptide in which a carboxyl group at the C-terminal of the peptide chain is protected by a carrier described later, while, an amino group at the N-terminal is not protected and is reactive.

The amino acid amide having a C-terminal protected by a carrier which is crystallized according to a change of a composition of a dissolving solvent (C-carrier protected amino acid amide) denotes an amino acid amide in which a carboxyl group thereof is protected by a carrier described later, while, an amino group is not protected and is reactive.

When the C-carrier protected amino acid or C-carrier protected peptide or C-carrier amino acid amide has a functional group rich in reactivity such as a hydroxyl group, an amino group, a guanidyl group, a carboxyl group, a sulfhydryl group and the like, a general protective group used in peptide chemistry may be introduced into these functional groups, and after completion of the reaction, the protective group is removed if necessary, thus, the target compound can be obtained.

The protective group for a hydroxyl group includes a tBu group, a Trt group, a Bz group, an acetyl group, a silyl group and the like, the protective group for an amino group includes a Boc group, a Fmoc group, a Cbz group, a Trt group, an Mmt group, an ivDde group and the like, the protective group for a guanidyl group includes a Pbf group, a Pmc group, a nitro group and the like, the protective group for a carboxyl group includes a tBu group, a methyl group, an ethyl group, a Bz group and the like, and the protective group for a sulfhydryl group includes a Trt group, an Acm group, a tBu group, an S-tBu group and the like.

3. Carrier which is Crystallized According to Change of Composition of Dissolving Solvent The carrier which is crystallized according to a change of a composition of a dissolving solvent denotes a carrier showing a reversible change between the dissolved state and the solidified (crystallized) state according to a change of the composition of the solvent dissolving the carrier. Specific examples thereof include, but not limited to, the following compounds, and a C-carrier protected amino acid, a C-carrier protected peptide or a C-carrier protected amino acid amide in which the C-terminal is protected by the carrier, used in the present invention, can be produced by bonding these compounds to the C-terminal of a peptide or an amino acid.

3-1. Carrier A

A compound having the following structure (in the present specification, referred to as "Ka" in some cases):

[Chemical Formula 16]

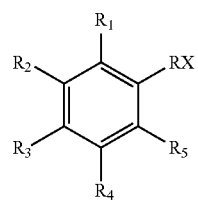

(wherein, $R_1$ and $R_5$ represent a hydrogen atom, and $R_2$, $R_3$ and $R_4$ represent an alkoxyl group having 8 to 30 carbon atoms. In the formula, RX is a group represented by the following formula and bonding to the C-terminal of a peptide or an amino acid,

[Chemical Formula 17]

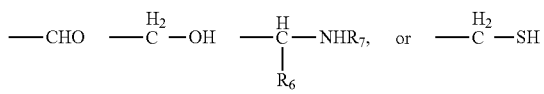

(wherein, $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group)).

In the above-described formula, $R_2$, $R_3$ and $R_4$ have a number of carbon atoms of more preferably 8 to 22, further preferably 12 to 18.

In the above-described formula, RX is more preferably a hydroxymethyl group, an aminomethyl group or a mercaptomethyl group, further preferably a hydroxymethyl group.

The compound included in the above-described formula is preferably 3,4,5-trioctadecylbenzyl alcohol, 3,4,5-trioctadecylbenzylamine or 3,4,5-trioctadecylbenzylthiol, further preferably 3,4,5-trioctadecylbenzyl alcohol or 3,4,5-trioctadecylbenzylamine, most preferably 3,4,5-trioctadecylbenzyl alcohol represented by the following formula.

[Chemical Formula 18]

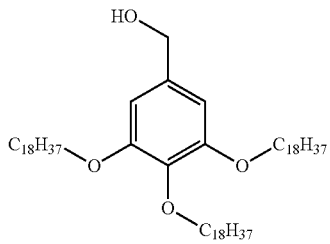

For bonding of the above-described compound to the C-terminal of a peptide or an amino acid, methods generally used in peptide synthesis can be used also in the present invention without restriction, and for example, the bonding can be carried out by esterification using DIPCI.

3-2. Carrier B

A compound having the following structure (in the present specification, referred to as "Kb" in some cases):

[Chemical Formula 19]

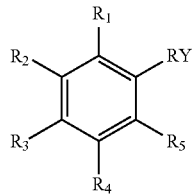

(wherein, $R_2$, $R_4$ and $R_5$ represent a hydrogen atom, and $R_1$ and $R_3$ represent an alkoxyl group having 12 to 30 carbon atoms. In the formula, RY is a group represented by the following formula and bonding to the C-terminal of a peptide or an amino acid,

[Chemical Formula 20]

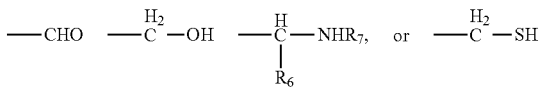

(wherein, $R_7$ represents a hydrogen atom, an alkyl group having 1 to 6 carbon atoms, a benzyl group, or an alkoxy-substituted benzyl group, and $R_6$ represents a hydrogen atom, a phenyl group or an alkoxy-substituted phenyl group)).

In the above-described formula, $R_1$ and $R_3$ more preferably have a number of carbon atoms of 18 to 22.

In the above-described formula, RX is more preferably a hydroxymethyl group, an aminomethyl group or a mercaptomethyl group, further preferably a hydroxymethyl group.

The compound included in the above-described formula is preferably 2,4-didocosyloxybenzyl alcohol, 2,4-didocosyloxybenzylamine or 2,4-didocosyloxybenzylthiol, further preferably 2,4-didocosyloxybenzyl alcohol or 2,4-didocosyloxybenzylamine, most preferably 2,4-didocosyloxybenzyl alcohol represented by the following formula.

[Chemical Formula 21]

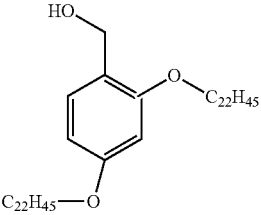

For bonding of the above-described compound to the C-terminal of a peptide or an amino acid, methods generally used in peptide synthesis can be used also in the present invention without restriction, and for example, the bonding can be carried out by esterification using DIPCI.

3-3. Carrier C

A compound having the following structure (in the present specification, referred to as "Kc" in some cases):

[Chemical Formula 22]

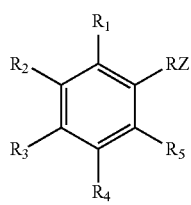

(wherein, $R_1$, $R_3$ and $R_5$ represent a hydrogen atom, and $R_2$ and $R_4$ represent an alkoxyl group having 12 to 30 carbon atoms. In the formula, RZ is a group represented by the following formula and bonding to the C-terminal of a peptide or an amino acid,

[Chemical Formula 23]

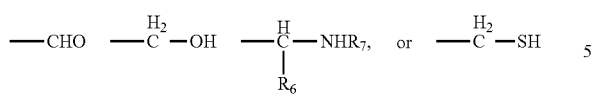

(wherein, $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group)), In the above-described formula, $R_2$ and $R_4$ more preferably have a number of carbon atoms of 18 to 22.

In the above-described formula, RX is more preferably a hydroxymethyl group, an aminomethyl group or a mercaptomethyl group, further preferably a hydroxymethyl group.

The compound included in the above-described formula is preferably 3,5-didocosyloxybenzyl alcohol, 3,5-didocosyloxybenzylamine or 3,5-didocosyloxybenzylthiol, further preferably 3,5-didocosyloxybenzyl alcohol or 3,5-didocosyloxybenzylamine, most preferably 3,5-didocosyloxybenzyl alcohol represented by the following formula.

[Chemical Formula 24]

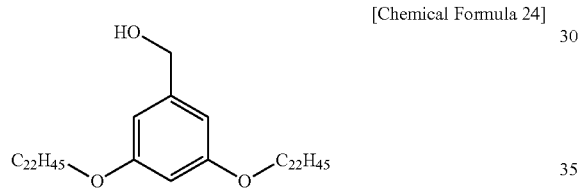

For bonding of the above-described compound to the C-terminal of a peptide or an amino acid, methods generally used in peptide synthesis can be used also in the present invention without restriction, and for example, the bonding can be carried out by esterification using DIPCI.

3-4. Carrier D

A compound having the following structure:

[Chemical Formula 25]

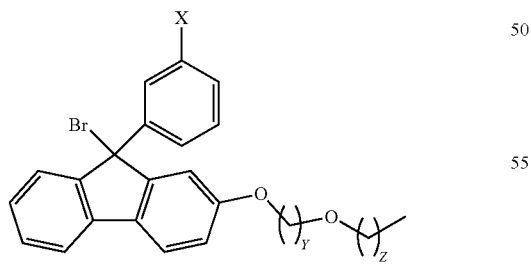

(wherein, X is a halogen, Y is an integer of 8 to 12 and Z is an integer of 17 to 29.).

In the above-described formula, X is preferably F or Cl, more preferably F.

A compound represented by the following formula is most preferable.

[Chemical Formula 26]

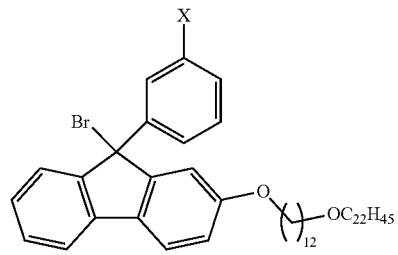

(wherein, X is F or Cl.)

For bonding of the above-described compound to the C-terminal of a peptide or an amino acid, methods generally used in peptide synthesis can be used also in the present invention without restriction, and for example, the bonding can be carried out by esterification using a basic catalyst.

3-5. Carrier E

A compound having the following structure:

[Chemical Formula 27]

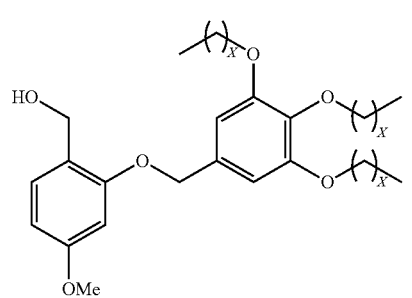

(wherein, X each independently represent an integer of 7 to 21.)

(2-(3,4,5-trioctadecyloxybenzyl)-4-methoxybenzyl alcohol represented by the following formula is most preferable.

[Chemical Formula 28]

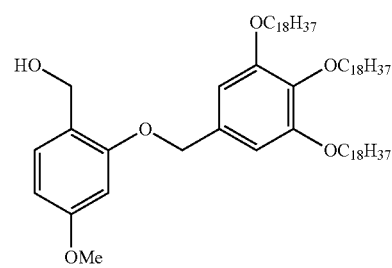

For bonding of the above-described compound to the C-terminal of a peptide or an amino acid, methods generally used in peptide synthesis can be used also in the present invention without restriction, and for example, the bonding can be carried out by esterification using DIPCI.

3-6. Carrier F

A compound having the following structure:

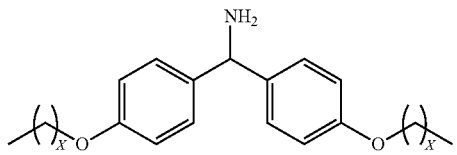

[Chemical Formula 29]

(wherein, X each independently represent an integer of 11 to 29.)

Bis-(4-docosyloxyphenyl)-methylamine represented by the following formula is most preferable.

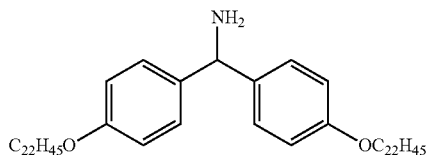

[Chemical Formula 30]

For bonding of the above-described compound to the C-terminal of a peptide or an amino acid, methods generally used in peptide synthesis can be used also in the present invention without restriction, and for example, the bonding can be carried out by amidation using DICPI/HOBt.

4. Production Method of Peptide

The peptide synthesis method of the present invention can be suitably used in a peptide production method using a carrier capable of reversibly repeating the dissolved state and the insolubilized state.

As the peptide production method including the peptide synthesis method of the present invention, for example, steps as shown below are exemplified.

(i) Coupling step a step of condensing an N-Fmoc protected amino acid or peptide with a C-carrier protected amino acid or peptide in the presence of a condensing agent, to obtain an N-Fmoc-C-carrier protected peptide, (ii) a step of forming a scavenged body of an amino acid active ester, using a primary or secondary alkylamine having 1 to 14 carbon atoms or a primary or secondary aromatic amine having 1 to 14 carbon atoms or hydroxylamine (hereinafter, referred to as amine scavenger), (iii) a step of removing an Fmoc group from the N-terminal of a peptide, to de-protect the N-terminal, (iv) a step of crystallizing and separating a carrier to which a peptide is bonded (C-carrier protected peptide), using a poor solvent, (v) a step of repeating the above-described steps (i) to (v) necessary times, and (vi) a step of removing the carrier from a peptide, to conduct final de-protection.

Further, after the above-described step (iv), (vii) a step of washing the crystallized and separated C-carrier protected peptide with an organic solvent, can also be added, and by this, removal of impurities including the scavenged body of an amino acid active ester is more complete.

The respective steps will be explained below.

4-1. Coupling Step

In this step, for example, an N-Fmoc protected amino acid is mixed with a C-carrier protected peptide, a C-carrier protected amino acid or a C-carrier protected amino acid amide and a condensing agent (preferably, a condensing agent and an activating agent) in a solvent, to obtain an N-Fmoc-C-carrier protected peptide in which one amino acid residue is elongated. If an N-Fmoc protected peptide is used instead of the N-Fmoc protected amino acid, an N-Fmoc-C-carrier protected peptide in which amino acid residues are elongated by the number of amino acid residues of the N-Fmoc protected peptide is obtained.

The method and order of addition of respective components are not particularly restricted, and methods usually used in a coupling step in peptide synthesis can be used.

The use amount of an N-Fmoc protected amino acid or an N-Fmoc protected peptide with respect to a C-protected carrier peptide is usually 1.03 to 8 equivalents, preferably 1.01 to 4 equivalents, more preferably 1.05 to 2 equivalents, further preferably 1.1 to 1.5 equivalents with respect to a C-carrier protected peptide and the like. Below this range, an unreacted C-protected peptide and the like tend to remain, and deletion of an amino acid occurs easily. In the peptide synthesis method of the present invention, unreacted amino acid active esters are scavenged (captured) by an amine scavenger to be added later, and they can be removed easily using an organic solvent, after de-protection of the N-terminal of an N-Fmoc-C-carrier protected peptide. Thus, even if a larger amount of an N-Fmoc protected amino acid or N-Fmoc protected peptide is used, the problem of remaining materials does not occur as compared with conventional methods.

As the condensing agent, condensing agents generally used in peptide synthesis can be used without restriction also in the present invention, and examples thereof include, but not limited to, 4-(4,6-dimethoxy-1,3,5-triazin-2-yl)-4-methylmorphonium chloride (DMT-MM), O-(benzotriazol-1-yl)-1,1,3,3-tetramethyluroniumhexafluoro phosphate (HBTU), O-(7-azabenzotriazol-1-yl)-1,1,3,3-tetramethyluroniumhexafluoro phosphate (HATU), O-(6-chlorobenzotriazol-1-yl)-1,1,3,3-tetramethyluroniumhexafluoro phosphate (HBTU (6-Cl)), O-(benzotriazol-1-yl)-1,1,3,3-tetramethyluroniumtetrafluoro borate (TBTU), O-(6-chlorobenzotriazol-1-yl)-1,1,3,3-tetramethyluroniumtetrafluoro borate (TCTU), (1-cyano-2-ethoxy-2-oxoethylideneaminooxy)dimethylamino-morpholino-carbeniumhexafluoro phosphate (COMU), diisopropylcarbodiimide (DIPCI), dicyclohexylcarbodiimide (DCC) and 1-ethyl-3-(3-dimethylaminopropyl)carbodiimide hydrochloride (WSC), and preferable is DMT-MM, HBTU, HATU or COMU. The use amount of the condensing agent is usually 0.7 to 1.5 equivalents, preferably 0.85 to 1.0 equivalents with respect to an N-Fmoc protected amino acid.

In the coupling step, an activating agent is preferably added for promoting the reaction and suppressing side reactions such as racemization and the like. The activating agent is a reagent converting an amino acid to the corresponding active ester, symmetric acid anhydride or the like, thereby facilitating formation of a peptide bond (amide bond), by coexistence with a condensing agent. As the activating agent, activating agents generally used in peptide synthesis can be used without restriction also in the present invention, and examples thereof include HOBt, HOCt, HOAt, HOOBt, HOSu, HOPht, HONb, pentafluorophenol and the like, and preferable are HOBt, HOOBt, HOCt, HOAt, HONb and HOSu. The use amount of the activating agent is usually 0 to 4.0 equivalents, preferably 0.1 to 1.5 equivalents with respect to an N-Fmoc amino acid.

As the solvent used in the coupling step, solvents generally used in peptide synthesis can be used without restriction also in the present invention, and examples thereof include, but not limited to, DMF, NMP, ethyl acetate, THF, acetonitrile, chloroform, methylene chloride, mixed solvents thereof, and the like, and preferable are THF, DMF or mixtures thereof. The use amount of the solvent is such an amount that the concentration of dissolution of a C-carrier protected peptide or the like is usually 0.3 M to 0.1 mM, preferably 0.2 M to 1 mM.

As the reaction temperature, temperatures generally used in peptide synthesis are used also in the present invention, and for example, it is in a range of usually −20 to 40° C., preferably 0 to 30° C. The reaction time (one cycle) is usually 0.5 to 30 hours.

4-2. Step of Forming Scavenged Body of Amino Acid Active Ester by Amine Scavenger The peptide production method using the present invention is characterized in that after an amino acid coupling step, an amine scavenger is added to the reaction system, and unreacted amino acid active esters are scavenged (captured).

The amine scavenger which can be used in the present invention includes primary or secondary alkylamines, primary or secondary aromatic amines or hydroxylamine. The alkylamine which can be used in the present invention includes, but not limited to, for example, alkylamines having 1 to 14 carbon atoms, and alkylamines having 2 to 10 carbon atoms are preferable, alkylamines having 2 to 8 carbon atoms are more preferable, alkylamines having 3 to 4 carbon atoms are further preferable. The aromatic amine which can be used in the present invention includes, for example, aromatic amines having 1 to 14 carbon atoms, and preferable are aromatic amines having 6 to 10 carbon atoms. Specific amine scavengers include, but not limited to, for example, propylamine, methylamine, hexylamine, aniline, toluidine, 2,4,6-trimethylaniline, anisidine, phenetidine and hydroxylamine, and particularly preferable is propylamine.

The addition amount of the amine scavenger is usually 1 to 30 equivalents, preferably 1 to 15 equivalents, more preferably 2 to 6 equivalents, further preferably 3 to 4 equivalents with respect to the equivalent of the theoretically remaining amino acid. When the addition amount of the amine scavenger is lower than this range, scavenging (capturing) of amino acid active esters becomes insufficient, and an N-Fmoc protected amino acid or peptide cannot be easily removed in the subsequent step, while when the amount is higher than this range, removal of unreacted amine scavengers becomes difficult.

4-3. N-Terminal De-Protection Step

In the peptide production method using the method of the present invention, removal of an Fmoc group from an N-Fmoc-C-carrier protected peptide is conducted after scavenging (capturing) an amino acid active ester in the reaction system by an amine scavenger, to form a scavenged body. For removal an Fmoc group from the N-terminal, removal methods generally used in peptide synthesis can be used without restriction also in the present invention. Removal can be conducted using, for example, DBU and piperidine, but the method is not limited to this. After this procedure, water washing with an ammonium chloride aqueous solution, a sodium chloride aqueous solution or both the solutions may be carried out.

4-4. Step of Crystallization and Separation of Carrier Protected Peptide

In the peptide production method using the method of the present invention, a C-carrier protected peptide from which an Fmoc group has been removed can be insolubilized (crystallized) and separated. Insolubilization can be carried out by changing a composition of a solution dissolving a C-carrier protected peptide. Conditions for insolubilization (crystallization) can be appropriately selected depending on the kind of a carrier to be used and the kind and the length of the synthesized C-carrier protected peptide. Examples thereof include, but not limited to, means as shown below.

(Composition Changing Means)

As the means for changing the composition of a solution which is preferably used in the method of the present invention, means capable of changing a composition of a solution dissolving a C-carrier protected peptide are used without particular restriction. The preferable means for changing a composition of a solution includes, for example, means in which a poor solvent is added to a solution dissolving a C-carrier protected peptide as it is or a poor solvent is added after concentrating the solvent of the solution, to cause crystallization. Here, concentrating means to distill off a part or all of the solvent. Thereafter, the precipitated crystal can be separated, for example, by filtration and centrifugal separation. Impurities separated together with the crystal can be removed completely from the crystallized C-carrier protected peptide, preferably by washing the separated crystal with an organic solvent.

The poor solvent used in the present invention means a solvent in which a C-protected amino acid amide is poorly soluble, that it, a C-protected amino acid amide is not dissolved easily or is not dissolved. For "C-protected amino acid amide is not dissolved easily or is not dissolved", the poor solvent may advantageously be a solvent which is liquid at normal temperature with which the solubility of a C-protected amino acid amide is less than 1% by mass at 25° C., and preferable are acetonitrile, any proportioned aqueous acetonitrile, methanol, any proportioned aqueous methanol and water.

As described above, a process from the condensation reaction (coupling reaction) to the de-protection reaction can be carried out in 1 pot synthesis, if the method of the present invention is used.

4-5. Final De-Protection Step

By removing a carrier at the C-terminal of a C-carrier protected peptide having a desired number of amino acid residues in the final de-protection step, a peptide as the final target can be obtained.

The method of removing a carrier at the C-terminal is not particularly restricted, and de-protection methods known per se may be used.

For example, a de-protection method using TFA can be used, and more specifically, it is preferable to perform de-protection with 50 to 100% trifluoroacetic acid when Ka is used, with 1 to 100% trifluoroacetic acid when Kb is used, with 95 to 100% trifluoroacetic acid when Kc is used, with 1 to 100% trifluoroacetic acid when carrier D and carrier E are used, and with 95 to 100% trifluoroacetic acid when carrier F is used.

The resultant peptide as the final target can be isolated and purified according to methods normally used in peptide chemistry. For example, the reaction mixture can be subjected to extraction washing, crystallization, chromatography and the like, to isolate and purify a peptide as the final target.

Though the kind of a peptide to be produced by the peptide synthesis method of the present invention is not particularly restricted, it is preferable that the number of amino acid residues of the peptide is, for example, around dozens or lower. The peptide obtained by the peptide synthesis method of the present invention can be used in various fields like existing or unknown synthetic peptides and natural peptides, and the fields include, but not limited to, for example, medicines, foods, cosmetics, electronic materials and the like.

EXAMPLES

The synthesis method is shown below using peptides having sequences shown below by way of examples, but the present invention is not limited to them.

(peptide A) H-Lys(Boc)Ala-Okb (peptide B) Fmoc-Gly-Arg(Pbf)-Met-Asp(OtBu)-Arg(Pbf)-Ile-Gly-OH (SEQ ID No. 1).

(peptide C) H-Gln(Trt)-Ser($\varphi_{Me}$, $_{Me}$ Pro)-Gly-Leu-Gly-Cys(Trt)-Asn(Trt)-Ser(tBu)-Phe-Arg(Pbf)-Tyr(tBu)-OKb (SEQ ID No. 2).

(peptide D) H-D-Arg-Arg-Pro-Hyp-Gly-Thi-Ser-D-Tic-Oic-Arg-OH (peptide E) H-Ala-Gln(Trt)-Ser($\varphi_{Me}$, $_{Me}$ Pro)-Gly-Leu-Gly-Cys(Trt)-Asn(Trt)-Ser(tBu)-Phe-Arg(Pbf)-Tyr(tBu)-Leu-OKb (SEQ ID No. 3).

(peptide F) Fmoc-Ser(tBu)-Leu-Arg(Pbf)-Arg(Pbf)-Ser(tBu)-Ser(tBu)-Cys(Trt)-Phe-Gly-OH (SEQ ID No. 4).

(peptide G) HCl.H-Ser(tBu)-Leu-Arg(Pbf)-Arg(Pbf)-Ser(tBu)-Ser(tBu)-Cys(Trt)-Phe-Gly-G-ly-Arg(Pbf)-Met-Asp(OtBu)-Arg(Pbf)-Ile-Gly-Ala-Gln(Trt)-Ser($\varphi_{Me}$, $_{Me}$ Pro)-Gly-Leu-Gly-Cys(Trt)-Asn(Trt)-Ser(tBu)-Phe-Arg(Pbf)-Tyr(tBu)-OKb (SEQ ID No. 5).

(peptide H) H-Ser-Leu-Arg-Arg-Ser-Ser-Ser-Phe-Gly-Gly-Arg-Met-Asp-Arg-Ile-Gly-Gln-Ser-Gly-Leu-Gly-Cys-Asn-Ser-Phe-Arg-Tyr-OH (7Cys-23Cys, SS bond) (SEQ ID No. 6).

(peptide I) H-Glu(OtBu)-Ile-Pro-Glu(OtBu)-Glu(OtBu)-Tyr(tBu)-Leu-OKb (SEQ ID No. 7).

(peptide J) Fmoc-Gly-Gly-Asn(Trt)-Gly-Asp(OtBu)-Phe-Glu(OtBu)-OH (SEQ ID No. 8).

(peptide K) Fmoc-D-Phe-Pro-Arg(Pbf)-Pro-Gly-Gly-OH (peptide L) H-D-Phe-Pro-Arg(Pbf)-Pro-Gly-Gly-Gly-Gly-Asn(Trt)-Gly-Asp(OtBu)-Phe-Glu(OtBu)-Glu(OtBu)-Ile-Pro-Glu(OtBu)-Glu(OtBu)-Tyr(tBu)-Leu-OKb (peptide M) H-D-Phe-Pro-Arg-Pro-Gly-Gly-Gly-Gly-Asn-Gly-Asp-Phe-Glu-Glu-Ile-Pro-Glu-Glu-Tyr-Leu-OH (peptide N) H-Lys(Boc)-Pro-Pro-Ala-Lys(Boc)-Leu-Gln(Trt)-Pro-Arg(Pbf)-OKb (SEQ ID No. 9).

(peptide O) Fmoc-Lys(Boc)Leu-Gln(Trt)-Gln(Trt)-Arg(pbf)-Lys(Boc)-Glu(OtBu)-Ser(tBu)-Lys(Boc)-OH (SEQ ID No. 10).

(peptide P) Boc-Gly-Ser(tBu)-Ser(n-Octanoyl)-Phe-Leu-Ser(tBu)-Pro-Glu(OtBu)-His(Trt)-Gln(Trt)-OH (SEQ ID No. 11).

(peptide Q) Boc-Gly-Ser(tBu)-Ser(n-Octanoyl)-Phe-Leu-Ser(tBu)-Pro-Glu(OtBu)-His(Trt)-Gln(Trt)-Lys(Boc)-Leu-Gln(Trt)-Gln(Trt)-Arg(pbf)-Lys(Boc)-Glu(OtBu)-Ser(tBu)-Lys(Boc)-Lys(Boc)-Pro-Pro-Ala-Lys(Boc)-Leu-Gln(Trt)-Pro-Arg(Pbf)-OKb (SEQ ID No. 12).

(peptide R) H-Gly-Ser-Ser(n-Octanoyl)-Phe-Leu-Ser-Pro-Glu-His-Gln-Lys-Leu-Gln-Gln-Arg-Lys-Glu-Ser-Lys-Lys-Pro-Pro-Ala-Lys-Leu-Gln-Pro-Arg-OH (SEQ ID No. 13).

In the present specification and examples described below, the following abbreviations are used.

AAs: one or more any amino acid residues
AAx: any amino acid residue
Boc: tert-butoxycarbonyl COMU (1-cyano-2-ethoxy-2-oxoethylideneaminooxy)dimethylamino-morpholino-carbeniumhexafluoro phosphate
CPME: cyclopentyl methyl ether
DBU: 1,8-diazabicyclo[5.4.0]-7-undecene
DCM: dichloromethane
DIPCI: diisopropylcarbodiimide
DMAP: N,N-dimethyl-4-aminopyridine
DMF: N,N-dimethylformamide
DMT-MM: 4-(4,6-dimethoxy-1,3,5-triazin-2-yl)-4-methylmorphonium chloride
EDT: 1,2-ethanedithiol
HATU: O-(7-azabenzotriazol-1-yl)-1,1,3,3-tetramethyluroniumhexafluoro phosphate
HBTU: O-(benzotriazol-1-yl)-1,1,3,3-tetramethyluroniumhexafluoro phosphate
HOAt: 1-hydroxy-7-azabenzotriazole
HOBt: 1-hydroxybenzotriazole
Ka: 3,4,5-trioctadecyloxybenzyl
Kb: 2,4-didocosyloxybenzyl
Kc: 3,5-didocosyloxybenzyl
Me: methyl
Oxyma: cyano(hydroxyimino)ethyl acetate
Pbf: 2,2,4,6,7-pentamethyldihydrobenzofuran-5-sulfonyl
Su: succinimidyl
tBu: tert-butyl
TFA: trifluoroacetic acid
TFE: 2,2,2-trifluoroethanol
THF: tetrahydrofuran
TIS: triisopropylsilane
WSC.HCl: 1-ethyl-3-(3-dimethylaminopropyl)carbodiimide hydrochloride (General Synthesis Method)
General synthesis methods used in the present examples are shown below.

(1) De-Fmoc(Fmoc-Deletion) General Synthesis Method

[Chemical Formula 31]

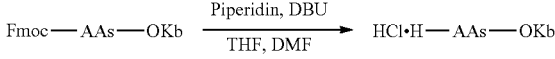

A starting raw material was dissolved in a mixture of THF:DMF (9/1) so as to give a concentration of 0.05 M, and piperidine (1.5 equiv) and DBU (1 equiv) were added and the mixture was stirred at room temperature for 10 minutes. Concentrated hydrochloric acid was added until pH of the reaction mixture became around 6 and the solvent was distilled off under reduced pressure. To the residue was added a mixture of acetonitrile:water=9:1 and the deposited precipitate was filtrated, and suspended and washed with a mixed liquid of acetonitrile:water=9:1, further, suspension washing with acetonitrile was conducted, and the resultant solid was dried under reduced pressure, to obtain a de-Fmoc body.

(2) Amino Acid Condensation General Synthesis Method

[Chemical Formula 32]

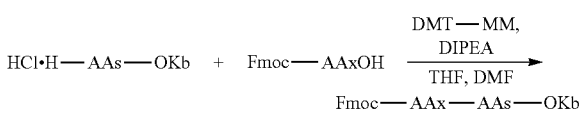

Starting raw materials were dissolved in a mixture of THF:DMF (9/1) so as to give a concentration of 0.05 M, and Fmoc-AAx-OH (1.3 equiv), DMT-MM (1.13 equiv) and DIPEA (1.2 equiv) were added and the mixture was stirred at room temperature for 30 minutes. The solvent was distilled off under reduced pressure, to the residue was added acetonitrile and the deposited precipitate was filtrated, suspension washing with acetonitrile was conducted twice, and the resultant solid was dried under reduced pressure, to obtain an amino acid condensate.

De-protection methods in the presence of an amine scavenger characteristic in the method of the present invention, used in the examples of the present invention, are shown below. Examples using propylamine as an example of the amine scavenger are shown.

(3) 1 Pot Condensation De-Protection Method with Addition of Amine Scavenger

[Chemical Formula 33]

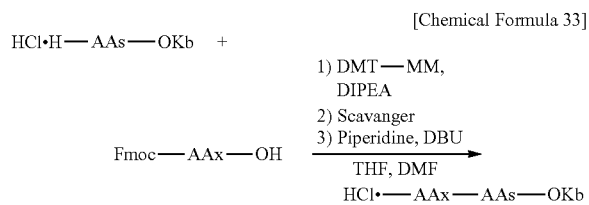

Starting raw materials were dissolved in a mixture of THF:DMF (9/1) so as to give a concentration of 0.05 M, and Fmoc-AAx-OH (1.3 equiv), DMT-MM (1.13 equiv) and DIPEA (1.13 equiv) were added and the mixture was stirred at room temperature for 30 minutes. As the amine scavenger, propylamine (1.2 equiv) was added and the mixture was stirred at room temperature for 30 minutes. HOBT (1 equiv), piperidine (1.5 equiv) and DBU (8 equiv) were added and the mixture was stirred at room temperature for 10 minutes. Concentrated hydrochloric acid was added until pH of the reaction mixture became around 6 and the solvent was distilled off under reduced pressure. To the residue was added a mixed liquid of acetonitrile:water=1:1 and the deposited precipitate was filtrated, and suspended and washed with a mixture of acetonitrile:water=9:1, further, suspension washing with acetonitrile was conducted, and the resultant solid was dried under reduced pressure, to obtain an amino acid condensate.

(4) 1 Pot Condensation De-Protection Method in which Amine Scavenger is Added and Washing with Ammonium Chloride Aqueous Solution is Conducted

[Chemical Formula 34]

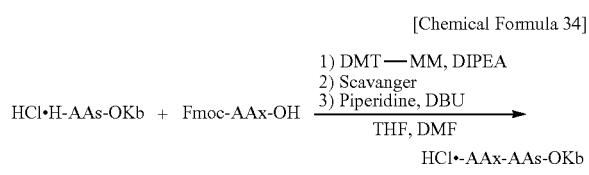

Starting raw materials were dissolved in a mixed liquid of THF:DMF (9/1) so as to give a concentration of 0.05 M, and Fmoc-AAx-OH (1.3 equiv), DMT-MM (1.13 equiv) and DIPEA (1.13 equiv) were added and the mixture was stirred at room temperature for 30 minutes. As the amine scavenger, propylamine (1.2 equiv) was added and the mixture was stirred at room temperature for 30 minutes. HOBT (1 equiv), piperidine (1.5 equiv) and DBU (8 equiv) were added and the mixture was stirred at room temperature for 10 minutes. Concentrated hydrochloric acid was added until pH of the reaction mixture became around 6. A solution of saturated ammonium chloride aqueous solution:water=1:2 of double amount of the reaction solvent was added to the reaction mixture, and the liquid was washed and separated, and the aqueous layer was discarded. Further, a solution of saturated saline:water=1:2 of double amount of the reaction solvent was added, and the liquid was washed and separated, and the aqueous layer was discarded. Further, saturated saline of double amount of the reaction solvent was added, and the liquid was washed and separated, and the aqueous layer was discarded. The resultant organic layer was held under reduced pressure and the solvent was distilled off. To the residue was added a mixture of acetonitrile:water=1:1 and the deposited precipitate was filtrated, and suspended and washed with a mixture of acetonitrile:water=9:1, further, suspension washing with acetonitrile was conducted, and the resultant solid was dried under reduced pressure, to obtain an amino acid condensate.

Next, a method of de-protecting (cutting) a carrier used in the present invention from a peptide is shown.

(5) Kb Protective Group General De-Protection Method

[Chemical Formula 35]

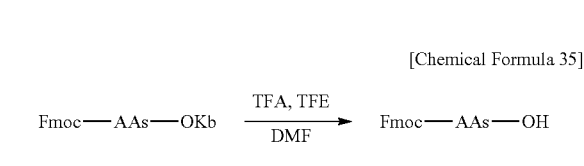

A raw material was dissolved in DCM so as to give a concentration of 0.01 M, and TFE of 1/10 amount of the DCM was added, further, TFA of 1/100 amount of the DCM was added and the mixture was stirred at room temperature for 30 minutes. The precipitate was filtrated, and the filtrate was adjusted to pH=9 with DIPEA, and the solvent was distilled off under reduced pressure. To the residue was added water and the deposited precipitate was filtrated, the resultant solid was dissolved in THF and toluene, then, distillation off under reduced pressure was performed. Suspension washing with addition of diisopropyl ether to the resultant solid was repeated three times, and the resultant solid was dried under reduced pressure, to obtain a de-Kb protected body.

Peptide synthesis using the method of the present invention is shown below.

(Example 1) Synthesis of Intermediate (Compound 2)

Synthesis of Compound 1

[Chemical Formula 36]

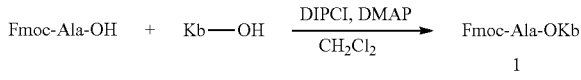

2,4-didocosyloxybenzyl alcohol (expressed as "Kb-OH") (3.79 g, 5.00 mmol) was dissolved in DCM (50 ml), and Fmoc-Ala-OH (2.34 g, 7.50 mmol, 1.5 equiv), DIPCI (1169 µL, 7.50 mmol, 1.5 equiv) and DMAP (31 mg, 0.25 mmol, 0.05 equiv) were added and the mixture was stirred at room temperature for 30 minutes. Propylamine (411 µL, 5.00 mmol, 1.0 equiv) was added and the mixture was stirred at room temperature for 30 minutes. The precipitate was filtrated, and the filtrate was distilled off under reduced pressure. To the residue was added MeOH and the deposited precipitate was filtrated, suspension washing with MeOH was conducted twice, suspension washing with acetonitrile was conducted, and the resultant solid was dried under reduced pressure, to obtain a compound 1 (5.02 g, 95.5%).

Synthesis of Compound 2

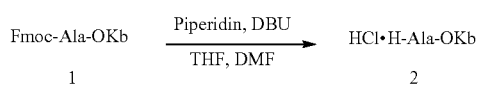

The compound 1 (5.00 g, 4.76 mmol) was dissolved in a mixture of THF (86 ml) and DMF (10 ml), and piperidine (707 µL, 7.14 mmol, 1.5 equiv) and DBU (712 µL, 4.76 mmol, 1 equiv) were added and the mixture was stirred at room temperature for 10 minutes. Concentrated hydrochloric acid was added until pH of the reaction mixture became around 6 and the solvent was distilled off under reduced pressure. To the residue was added a mixture of acetonitrile:water=9:1 and the deposited precipitate was filtrated, and suspended and washed with a mixture of acetonitrile:water=9:1, further, suspension washing with acetonitrile was conducted, and the resultant solid was dried under reduced pressure, to obtain a compound 2 (4.05 g, 98.3%).

(Comparative Example 1) Two-Step Synthesis of H-Lys(Boc)Ala-OKb (Compound 4)

Synthesis of Compound 3

[Chemical Formula 37]

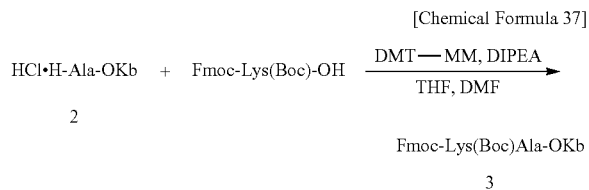

The compound 2 (86 mg, 0.1 mmol) obtained in Example 1 was dissolved in a mixture of THF (2 ml) and DMF (0.2 ml), and Fmoc-Lys(Boc)-OH (61 mg, 0.13 mmol, 1.3 equiv), DMT-MM (32 mg, 0.113 mmol, 1.13 equiv) and DIPEA (21 µL, 0.12 mmol, 1.2 equiv) were added and the mixture was stirred at room temperature for 30 minutes. The solvent was distilled off under reduced pressure, to the residue was added acetonitrile and the deposited precipitate was filtrated, suspension washing with acetonitrile was conducted twice, and the resultant solid was dried under reduced pressure, to obtain a compound 3 (128.5 mg, quant).

Synthesis of Compound 4

[Chemical Formula 38]

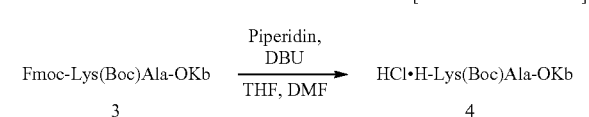

The compound 3 (119 mg, 0.093 mmol) was dissolved in a mixture of THF (2 ml) and DMF (0.2 ml), and piperidine (14 µL, 0.14 mmol, 1.5 equiv) and DBU (28 µL, 0.28 mmol, 2 equiv) were added and the mixture was stirred at room temperature for 10 minutes. Concentrated hydrochloric acid was added until pH of the reaction mixture became around 6 and the solvent was distilled off under reduced pressure. To the residue was added a mixture of acetonitrile:water=1:1 and the deposited precipitate was filtrated, and suspended and washed with a mixture of acetonitrile:water=9:1, further, suspension washing with acetonitrile was conducted, and the resultant solid was dried under reduced pressure, to obtain a compound 4 (92.5 mg, 90.7%).

(Example 2) Synthesis of H-Lys(Boc)Ala-OKb (Compound 4) with Addition of Amine Scavenger—(1)

[Chemical Formula 39]

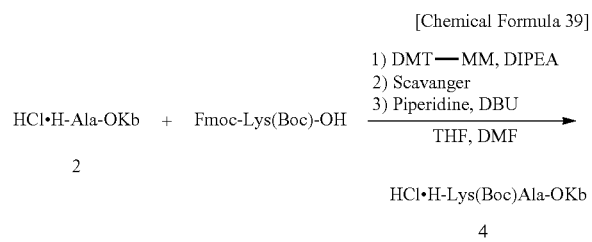

The compound 2 (173 mg, 0.2 mmol) obtained in Example 1 was dissolved in a mixture of THF (4 ml) and DMF (0.4 ml), and Fmoc-Lys(Boc)-OH (122 mg, 0.26 mmol, 1.3 equiv), DMT-MM (65 mg, 0.226 mmol, 1.13 equiv) and DIPEA (42 µL, 0.24 mmol, 1.2 equiv) were added and the mixture was stirred at room temperature for 30 minutes. As the amine scavenger, propylamine (19.7 µL, 0.24 mmol, 1.2 equiv) was added and the mixture was stirred at room temperature for 30 minutes. HOBT (30.6 mg, 0.26 mmol, 1 equiv), piperidine (30 µL, 0.3 mmol, 1.5 equiv) and DBU (239 µL, 1.6 mmol, 8 equiv) were added and the mixture was stirred at room temperature for 10 minutes. Concentrated hydrochloric acid was added until pH of the reaction mixture became around 6 and the solvent was distilled off under reduced pressure. To the residue was added a mixture of acetonitrile:water=1:1 and the deposited precipitate was filtrated, and suspended and washed with a mixture of acetonitrile:water=9:1, further, suspension washing with acetonitrile was conducted, and the resultant solid was dried under reduced pressure, to obtain a compound 4 (92.5 mg, 90.7%).

(Example 3) Synthesis of H-Lys(Boc)Lys(Boc)Ala-OKb (Compound 5) with Addition of Amine Scavenger

[Chemical Formula 40]

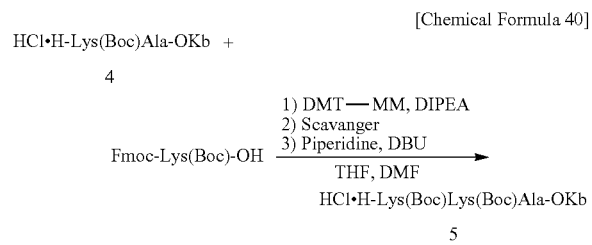

The compound 4 (109 mg, 0.1 mmol) obtained in Example 2 was dissolved in a mixture of THF (2 ml) and DMF (0.2 ml), and Fmoc-Lys(Boc)-OH (61 mg, 0.13 mmol, 1.3 equiv), DMT-MM (32 mg, 0.113 mmol, 1.13 equiv) and DIPEA (21 μL, 0.12 mmol, 1.2 equiv) were added and the mixture was stirred at room temperature for 30 minutes. As the amine scavenger, propylamine (9.9 μL, 0.12 mmol, 1.2 equiv) was added and the mixture was stirred at room temperature for 30 minutes. Piperidine (15 μL, 0.15 mmol, 1.5 equiv) and DBU (105 μL, 1.4 mmol, 7 equiv) were added and the mixture was stirred at room temperature for 10 minutes. After this, the same procedure as in Example 2 was conducted, to obtain a compound 5 (115.2 mg, 87.2%).

(Example 4) Synthesis of H-Lys(Boc)Ala-OKb (Compound 4) with Addition of Amine Scavenger—(2)

[Chemical Formula 41]

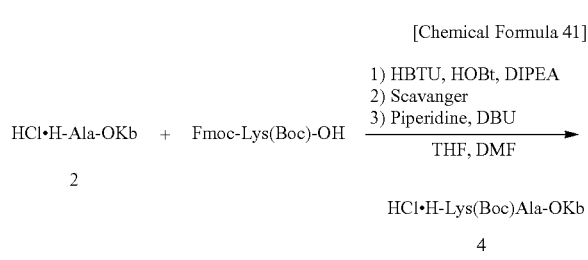

The compound 2 (86 mg, 0.1 mmol) obtained in Example 1 was dissolved in a mixture of THF (2 ml) and DMF (0.2 ml), and Fmoc-Lys(Boc)-OH (61 mg, 0.13 mmol, 1.3 equiv), HBTU (44 mg, 0.113 mmol, 1.13 equiv), HOBt (18 mg, 0.113 mmol, 1.13 equiv) and DIPEA (87 μL, 0.5 mmol, 5 equiv) were added and the mixture was stirred at room temperature for 30 minutes. As the amine scavenger, propylamine (9.9 μL, 0.12 mmol, 1.2 equiv) was added and the mixture was stirred at room temperature for 30 minutes. Piperidine (15 μL, 0.15 mmol, 1.5 equiv) and DBU (120 μL, 1.6 mmol, 8 equiv) were added and the mixture was stirred at room temperature for 10 minutes. After this, the same procedure as in Example 2 was conducted, to obtain a compound 4 (109.2 mg, 99.9%).

(Example 5) Synthesis of H-Lys(Boc)Ala-OKb (Compound 4) with Addition of Amine Scavenger—(3)

[Chemical Formula 42]

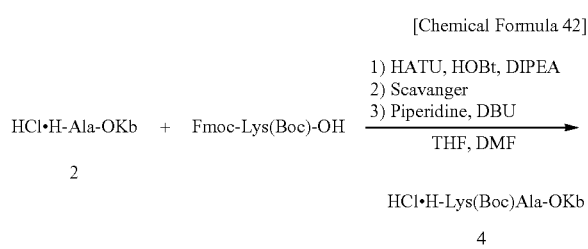

The compound 2 (86 mg, 0.1 mmol) obtained in Example 1 was dissolved in a mixture of THF (2 ml) and DMF (0.2 ml), and Fmoc-Lys(Boc)-OH (61 mg, 0.13 mmol, 1.3 equiv), HATU (44 mg, 0.113 mmol, 1.13 equiv), HOAt (16 mg, 0.113 mmol, 1.13 equiv) and DIPEA (87 μL, 0.5 mmol, 5 equiv) were added and the mixture was stirred at room temperature for 30 minutes. As the amine scavenger, propylamine (9.9 μL, 0.12 mmol, 1.2 equiv) was added and the mixture was stirred at room temperature for 30 minutes. Piperidine (15 μL, 0.15 mmol, 1.5 equiv) and DBU (120 μL, 1.6 mmol, 8 equiv) were added and the mixture was stirred at room temperature for 10 minutes. After this, the same procedure as in Example 2 was conducted, to obtain a compound 4 (103.5 mg, 94.7%).

(Example 6) Synthesis of H-Lys(Boc)Ala-OKb (Compound 4) with Addition of Amine Scavenger—(4)

[Chemical Formula 43]

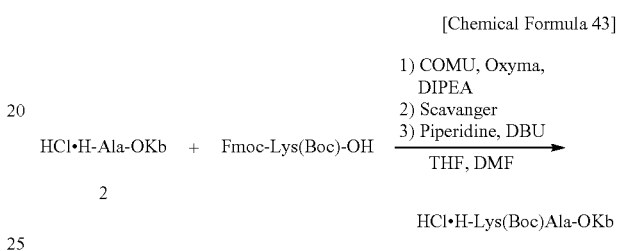

The compound 2 (86 mg, 0.1 mmol) obtained in Example 1 was dissolved in a mixture of THF (2 ml) and DMF (0.2 ml), Fmoc-Lys(Boc)-OH (61 mg, 0.13 mmol, 1.3 equiv), COMU (50 mg, 0.113 mmol, 1.13 equiv), Oxyma (17 mg, 0.113 mmol, 1.13 equiv) and DIPEA (87 μL, 0.5 mmol, 5 equiv) were added and the mixture was stirred at room temperature for 30 minutes. As the amine scavenger, propylamine (9.9 μL, 0.12 mmol, 1.2 equiv) was added and the mixture was stirred at room temperature for 30 minutes. Piperidine (15 μL, 0.15 mmol, 1.5 equiv) and DBU (120 μL, 1.6 mmol, 8 equiv) were added and the mixture was stirred at room temperature for 10 minutes. After this, the same procedure as in Example 2 was conducted, to obtain a compound 4 (105.7 mg, 96.7%).

(Example 7) Synthesis of H-Lys(Boc)Ala-OKb (Compound 4) with Addition of Amine Scavenger—(5)

The compound 2 (86 mg, 0.1 mmol) obtained in Example 1 was dissolved in a mixture of THF (2 ml) and DMF (0.1 ml), Fmoc-Lys(Boc)-OH (61 mg, 0.13 mmol, 1.3 equiv), DMT-MM (32 mg, 0.113 mmol, 1.13 equiv) and DIPEA (21 μL, 0.12 mmol, 1.2 equiv) were added and the mixture was stirred at room temperature for 30 minutes. As the amine scavenger, propylamine (2.5 μL, 0.03 mmol, 0.3 equiv) was added and the mixture was stirred at room temperature for 30 minutes. HOBT (30.6 mg, 0.26 mmol, 1 equiv), piperidine (30 μL, 0.3 mmol, 1.5 equiv) and DBU (239 μL, 1.6 mmol, 8 equiv) were added and the mixture was stirred at room temperature for 10 minutes. After this, the same procedure as in Example 2 was conducted, to obtain a compound 4 (105.3 mg, 96.3%).

(Example 8) Synthesis of H-Lys(Boc)Ala-OKb (Compound 4) with Addition of Amine Scavenger—(6)

The compound 2 (86 mg, 0.1 mmol) obtained in Example 1 was dissolved in a mixture of THF (2 ml) and DMF (0.1 ml), Fmoc-Lys(Boc)-OH (61 mg, 0.13 mmol, 1.3 equiv), DMT-MM (32 mg, 0.113 mmol, 1.13 equiv) and DIPEA (21 µL, 0.12 mmol, 1.2 equiv) were added and the mixture was stirred at room temperature for 30 minutes. As the amine scavenger, propylamine (4.9 µL, 0.06 mmol, 0.6 equiv) was added and the mixture was stirred at room temperature for 30 minutes. HOBT (30.6 mg, 0.26 mmol, 1 equiv), piperidine (30 µL, 0.3 mmol, 1.5 equiv) and DBU (239 µL, 1.6 mmol, 8 equiv) were added and the mixture was stirred at room temperature for 10 minutes. After this, the same procedure as in Example 2 was conducted, to obtain a compound 4 (105.6 mg, 96.6%).

(Example 9) Synthesis of H-Lys(Boc)Ala-OKb (Compound 4) with Addition of Amine Scavenger—(7)

The compound 2 (86 mg, 0.1 mmol) obtained in Example 1 was dissolved in a mixture of THF (2 ml) and DMF (0.1 ml), Fmoc-Lys(Boc)-OH (61 mg, 0.13 mmol, 1.3 equiv), DMT-MM (32 mg, 0.113 mmol, 1.13 equiv) and DIPEA (21 µL, 0.12 mmol, 1.2 equiv) were added and the mixture was stirred at room temperature for 30 minutes. As the amine scavenger, propylamine (19.7 µL, 0.24 mmol, 2.4 equiv) was added and the mixture was stirred at room temperature for 30 minutes. HOBT (30.6 mg, 0.26 mmol, 1 equiv), piperidine (30 µL, 0.3 mmol, 1.5 equiv) and DBU (239 µL, 1.6 mmol, 8 equiv) were added and the mixture was stirred at room temperature for 10 minutes. After this, the same procedure as in Example 2 was conducted, to obtain a compound 4 (105.6 mg, 96.6%).

(Example 10) Synthesis of H-Lys(Boc)Ala-OKb (Compound 4) with Addition of Amine Scavenger—(8)

The compound 2 (86 mg, 0.1 mmol) obtained in Example 1 was dissolved in a mixture of THF (2 ml) and DMF (0.1 ml), Fmoc-Lys(Boc)-OH (61 mg, 0.13 mmol, 1.3 equiv), DMT-MM (32 mg, 0.113 mmol, 1.13 equiv) and DIPEA (21 µL, 0.12 mmol, 1.2 equiv) were added and the mixture was stirred at room temperature for 30 minutes. As the amine scavenger, propylamine (37 µL, 0.45 mmol, 4.5 equiv) was added and the mixture was stirred at room temperature for 30 minutes. HOBT (30.6 mg, 0.26 mmol, 1 equiv), piperidine (30 µL, 0.3 mmol, 1.5 equiv) and DBU (239 µL, 1.6 mmol, 8 equiv) were added and the mixture was stirred at room temperature for 10 minutes. After this, the same procedure as in Example 2 was conducted, to obtain a compound 4 (105.2 mg, 96.2%).

(Example 11) Synthesis of H-Lys(Boc)Ala-OKb (Compound 4) with Addition of Amine Scavenger—(9)

The compound 2 (86 mg, 0.1 mmol) obtained in Example 1 was dissolved in a mixture of THF (2 ml) and DMF (0.1 ml), Fmoc-Lys(Boc)-OH (61 mg, 0.13 mmol, 1.3 equiv), DMT-MM (32 mg, 0.113 mmol, 1.13 equiv) and DIPEA (21 µL, 0.12 mmol, 1.2 equiv) were added and the mixture was stirred at room temperature for 30 minutes. As the amine scavenger, a 40% methylamine aqueous solution (10.3 µL, 0.12 mmol, 1.2 equiv) was added and the mixture was stirred at room temperature for 30 minutes. HOBT (30.6 mg, 0.26 mmol, 1 equiv), piperidine (30 µL, 0.3 mmol, 1.5 equiv) and DBU (239 µL, 1.6 mmol, 8 equiv) were added and the mixture was stirred at room temperature for 10 minutes. After this, the same procedure as in Example 2 was conducted, to obtain a compound 4 (101.6 mg, 93.0%).

(Example 12) Synthesis of H-Lys(Boc)Ala-OKb (Compound 4) with Addition of Amine Scavenger—(10)

The compound 2 (86 mg, 0.1 mmol) obtained in Example 1 was dissolved in a mixture of THF (2 ml) and DMF (0.1 ml), Fmoc-Lys(Boc)-OH (61 mg, 0.13 mmol, 1.3 equiv), DMT-MM (32 mg, 0.113 mmol, 1.13 equiv) and DIPEA (21 µL, 0.12 mmol, 1.2 equiv) were added and the mixture was stirred at room temperature for 30 minutes. As the amine scavenger, a 50% hydroxylamine aqueous solution (7.1 µL, 0.12 mmol, 1.2 equiv) was added and the mixture was stirred at room temperature for 30 minutes. HOBT (30.6 mg, 0.26 mmol, 1 equiv), piperidine (30 µL, 0.3 mmol, 1.5 equiv) and DBU (239 µL, 1.6 mmol, 8 equiv) were added and the mixture was stirred at room temperature for 10 minutes. After this, the same procedure as in Example 2 was conducted, to obtain a compound 4 (104.1 mg, 95.2%).

(Example 13) Synthesis of H-Lys(Boc)Ala-OKb (Compound 4) with Addition of Amine Scavenger—(11)

The compound 2 (86 mg, 0.1 mmol) obtained in Example 1 was dissolved in a mixture of THF (2 ml) and DMF (0.1 ml), Fmoc-Lys(Boc)-OH (61 mg, 0.13 mmol, 1.3 equiv), DMT-MM (32 mg, 0.113 mmol, 1.13 equiv) and DIPEA (21 µL, 0.12 mmol, 1.2 equiv) were added and the mixture was stirred at room temperature for 30 minutes. As the amine scavenger, hexylamine (15.9 µL, 0.12 mmol, 1.2 equiv) was added and the mixture was stirred at room temperature for 30 minutes. HOBT (30.6 mg, 0.26 mmol, 1 equiv), piperidine (30 µL, 0.3 mmol, 1.5 equiv) and DBU (239 µL, 1.6 mmol, 8 equiv) were added and the mixture was stirred at room temperature for 10 minutes. After this, the same procedure as in Example 2 was conducted, to obtain a compound 4 (104.6 mg, 95.7%).

(Example 14) Synthesis of H-Lys(Boc)Ala-OKb (Compound 4) with Addition of Amine Scavenger—(12)

The compound 2 (86 mg, 0.1 mmol) obtained in Example 1 was dissolved in a mixture of THF (2 ml) and DMF (0.1 ml), Fmoc-Lys(Boc)-OH (61 mg, 0.13 mmol, 1.3 equiv), DMT-MM (32 mg, 0.113 mmol, 1.13 equiv) and DIPEA (21 µL, 0.12 mmol, 1.2 equiv) were added and the mixture was stirred at room temperature for 30 minutes. As the amine scavenger, decylamine (15.9 µL, 0.12 mmol, 1.2 equiv) was added and the mixture was stirred at room temperature for 30 minutes. HOBT (30.6 mg, 0.26 mmol, 1 equiv), piperidine (30 µL, 0.3 mmol, 1.5 equiv) and DBU (239 µL, 1.6 mmol, 8 equiv) were added and the mixture was stirred at room temperature for 10 minutes. After this, the same procedure as in Example 2 was conducted, to obtain a compound 4 (107.5 mg, 98.4%).

(Comparative Example 2) Synthesis of H-Lys(Boc)Ala-OKb (Compound 4) with Addition of Amine Scavenger not Included in the Present Invention—(13)

The compound 2 (86 mg, 0.1 mmol) obtained in Example 1 was dissolved in a mixture of THF (2 ml) and DMF (0.1 ml), Fmoc-Lys(Boc)-OH (61 mg, 0.13 mmol, 1.3 equiv), DMT-MM (32 mg, 0.113 mmol, 1.13 equiv) and DIPEA (21 μL, 0.12 mmol, 1.2 equiv) were added and the mixture was stirred at room temperature for 30 minutes. As the amine scavenger, 2-aminoethanol (7.2 μL, 0.12 mmol, 1.2 equiv) was added and the mixture was stirred at room temperature for 30 minutes. HOBT (30.6 mg, 0.26 mmol, 1 equiv), piperidine (30 μL, 0.3 mmol, 1.5 equiv) and DBU (239 μL, 1.6 mmol, 8 equiv) were added and the mixture was stirred at room temperature for 10 minutes. After this, the same procedure as in Example 2 was conducted, to obtain a compound 4 (103.6 mg, 94.8%).

(Example 15) Synthesis of H-Lys(Boc)Ala-OKb (Compound 4) with Addition of Amine Scavenger—(14)

The compound 2 (86 mg, 0.1 mmol) obtained in Example 1 was dissolved in a mixture of THF (2 ml) and DMF (0.1 ml), Fmoc-Lys(Boc)-OH (187 mg, 0.4 mmol, 4.0 equiv), DMT-MM (100 mg, 0.36 mmol, 3.6 equiv) and DIPEA (21 μL, 0.12 mmol, 1.2 equiv) were added and the mixture was stirred at room temperature for 30 minutes. As the amine scavenger, propylamine (99 μL, 1.2 mmol, 12 equiv) was added and the mixture was stirred at room temperature for 30 minutes. HOBT (30.6 mg, 0.26 mmol, 1 equiv), piperidine (30 μL, 0.3 mmol, 1.5 equiv) and DBU (239 μL, 1.6 mmol, 8 equiv) were added and the mixture was stirred at room temperature for 10 minutes. After this, the same procedure as in Example 2 was conducted, to obtain a compound 4 (104.2 mg, 95.3%).

(Example 16) Measurement of Purity of H-Ala-OKb (Compound 2), H-Lys(Boc)Ala-OKb (Compound 4) and H-Lys(Boc)Lys(Boc)Ala-OKb (Compound 5) by HPLC (1) Sample Preparation (Common)
Each 1 mg of the compounds obtained in Examples and Comparative Examples described above were weighed and dissolved in 0.5 mL of THF, and a 0.1M Fmoc-OSu THF solution (20 μL, 0.02 mmol, about 2 equiv) and a 0.2M DIPEA THF solution (10 μL, 0.02 mmol, about 2 equiv) were added and the mixtures were stirred at room temperature for 1 hour. After air drying, the solutions were suspended and washed with acetonitrile three times, and dried under reduced pressure. To the resultant solids was added 1 ml of THF for HPLC (containing no stabilizer) and the resultant solutions were filtrated through a 0.2 μm membrane filter, and the resultant filtrates were used as samples for HPLC and subjected to measurement of HPLC.

(2) HPLC Measurement
HPLC measurement was conducted according to the following conditions.
<Reverse Phase HPLC>
Column: reverse phase C4 column
Mobile phase A: THF:CH$_3$CN=8:2 mixture
Mobile phase B: 0.1% TFA-containing water
Flow rate: 0.2 ml/min
Gradient: A, from 70% to 100% over 30 minutes
Detection wavelength: 254 nm
<Normal Phase HPLC>
Column: normal phase silica gel column
Mobile phase A: ethyl acetate
Mobile phase B: n-hexane
Flow rate: 0.2 ml/min Gradient: mobile phase A, from 0% to 100% over 30 minutes
Detection wavelength: 280 nm
The results are shown in Table 1 below.

TABLE 1

| | Compound 2 contained amount (reverse phase) | Compound 4 contained amount (reverse phase) | Compound 5 contained amount (normal phase) |
|---|---|---|---|
| Example 1 | 99.35% | 0 | 0 |
| Comparative Example 1 | 0 | 99.46% | 0.05% |
| Example 2 | 0 | 99.12% | 0 |
| Example 3 | 0 | 0 | 100% |
| Example 4 | 0 | 98.36% | 0 |
| Example 5 | 0 | 99.03% | 0 |
| Example 6 | 0 | 99.29% | 0 |
| Example 7 | 0 | 99.78% | 0 |
| Example 8 | 0 | 99.71% | 0 |
| Example 9 | 0 | 99.78% | 0 |
| Example 10 | 0 | 99.74% | 0 |
| Example 11 | 0 | 99.29% | 0.03% |
| Example 12 | 0 | 99.31% | 0 |
| Example 13 | 0 | 98.26% | 0 |
| Example 14 | 0 | 99.21% | 0 |
| Example 15 | 0 | 98.42% | 0 |
| Comparative Example 2 | 0 | 99.54% | 0.20% |

(Example 17) Synthesis of HCl.H-Ile-Gly-OKb (Compound 14)

Synthesis of Compound 6

[Chemical Formula 44]

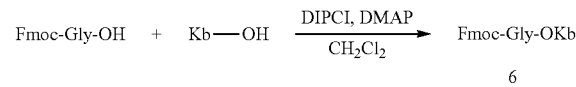

2,4-didocosyloxybenzyl alcohol (expressed as "KbOH") (1.51 g, 2.00 mmol) was dissolved in DCM (50 ml), Fmoc-Gly-OH (892 mg, 3.0 mmol, 1.5 equiv), DIPCI (467 μL, 3.0 mmol, 1.5 equiv) and DMAP (12 mg, 0.1 mmol, 0.05 equiv) were added and the mixture was stirred at room temperature for 30 minutes. The precipitate was filtrated, and the filtrate was distilled off under reduced pressure. To the residue was added MeOH and the deposited precipitate was filtrated, suspension washing with MeOH was conducted twice, suspension washing with acetonitrile was conducted, and the resultant solid was dried under reduced pressure, to obtain a compound 6 (2.01 g, 97.1%).

Synthesis of Compound 7

[Chemical Formula 45]

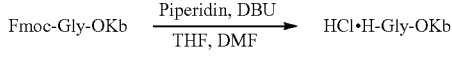

The resultant compound 6 (2.01 g, 0.1 mmol) was subjected to a de-Fmoc operation according to a de-Fmoc general synthesis method, to obtain a compound 7 (1.84 g, quant).

Synthesis of Compound 8

[Chemical Formula 46]

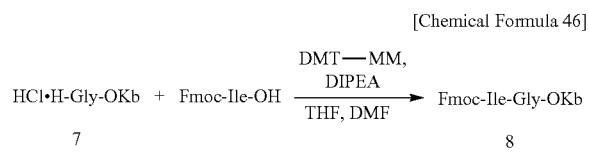

The resultant compound 7 (1.84 g, 0.1 mmol) was condensed with Fmoc-Ile-OH according to an amino acid general condensation method, to obtain a compound 8 (1.99 g, 88.9%).

Synthesis of Compound 9

[Chemical Formula 47]

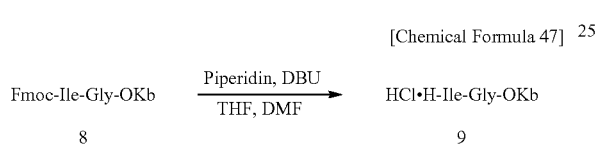

The resultant compound 8 (662 mg, 0.58 mmol) was subjected to a de-Fmoc operation according to a de-Fmoc general synthesis method, to obtain a compound 9 (505 mg, 91%).

(Comparative Example 3) Synthesis of Fmoc-Gly-Arg(Pbf)-Met-Asp(OtBu)-Arg(Pbf)-Ile-Gly-OKb (Compound 10)

The following amino acids were introduced into the compound 9 obtained in Example 17 by repeating an amino acid general condensation method and a de-Fmoc general synthesis method, to obtain a compound 10.
Third residue: Fmoc-Arg(Pbf)-OH
Fourth residue: Fmoc-Asp(OtBu)-OH
Fifth residue: Fmoc-Met-OH
Sixth residue: Fmoc-Arg(Pbf)-OH
Seventh residue: Fmoc-Gly-OH (Comparative Example 4) Synthesis of Fmoc-Gly-Arg(Pbf)-Met-Asp(OtBu)-Arg(Pbf)-Ile-Gly-OH (Compound 11)

The compound 10 obtained in Comparative Example 2 was subjected to a de-Kb operation according to a Kb protective group general de-protection method, to obtain a compound 11. The resultant compound was subjected to LC-MS measurement, to observe 1643.7 [M+Gly+H$^+$], 1995.2 [M+Arg(Pbf)+H$^+$], 1758.1 [M+Asp(OtBu)+H$^+$] and 1718.0 [M+Met+H$^+$].

(Example 18) Synthesis of Fmoc-Gly-Arg(Pbf)-Met-Asp(OtBu)-Arg(Pbf)-Ile-Gly-OKb (Compound 10) by 1 Pot Condensation De-Protection Method with Addition of Amine Scavenger The following amino acids were introduced into the compound 9 obtained in Example 17 by repeating a 1 pot condensation de-protection method with addition of an amine scavenger, to obtain a compound 10.
Introduction of
Third residue: Fmoc-Arg(Pbf)-OH
Fourth residue: Fmoc-Asp(OtBu)-OH
Fifth residue: Fmoc-Met-OH
Sixth residue: Fmoc-Arg(Pbf)-OH
Seventh residue: Fmoc-Gly-OH, which was conducted according to an amino acid general condensation method.

(Example 19) Synthesis of Fmoc-Gly-Arg(Pbf)-Met-Asp(OtBu)-Arg(Pbf)-Ile-Gly-OH (Compound 11)

The compound 10 obtained in Example 18 was subjected to a de-Kb operation according to a Kb protective group general de-protection method, to obtain a compound 11. The resultant compound was subjected to LC-MS measurement, but 1643.7 [M+Gly+H$^+$], 1995.2 [M+Arg(Pbf)+H$^+$], 1758.1 [M+Asp(OtBu)+H$^+$] and 1718.0 [M+Met+H$^+$] were not observed.

(Example 20) Synthesis of H-Gly-Leu-Gly-Cys(Trt)-Asn(Trt)-Ser(tBu)-Phe-Arg(Pbf)-Tyr(tBu)-Okb (Compound 14)

Synthesis of Compound 12

[Chemical Formula 48]

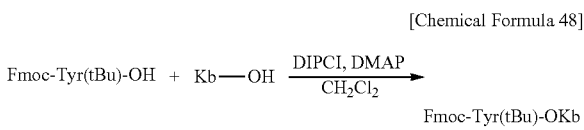

2,4-didocosyloxybenzyl alcohol (expressed as "Kb-OH") (3.79 g, 5.00 mmol) was dissolved in DCM (50 ml), Fmoc-Tyr(tBu)-OH (3.45 g, 7.50 mmol, 1.5 equiv), DIPCI (1169 μL, 7.50 mmol, 1.5 equiv) and DMAP (31 mg, 0.25 mmol, 0.05 equiv) were added and the mixture was stirred at room temperature for 30 minutes. Propylamine (811 μL, 10.0 mmol, 2.0 equiv) was added and the mixture was stirred at room temperature for 30 minutes. The precipitate was filtrated, and the filtrate was distilled off under reduced pressure. To the residue was added MeOH and the deposited precipitate was filtrated, suspension washing with MeOH was conducted twice, suspension washing with acetonitrile was conducted, and the resultant solid was dried under reduced pressure, to obtain a compound 12 (6.06 g, quant).

Synthesis of Compound 13

[Chemical Formula 49]

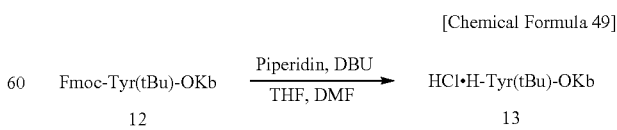

The compound 12 (6.06 g, 5.00 mmol) was dissolved in a mixture of THF (86 ml) and DMF (10 ml), piperidine (743 μL, 7.5 mmol, 1.5 equiv) and DBU (748 μL, 5.00 mmol, 1 equiv) were added and the mixture was stirred at room temperature for 10 minutes. Concentrated hydrochloric acid was added until pH of the reaction mixture became around 6. A solution of saturated saline:water=2:1 of double amount of the reaction solvent was added to the reaction mixture and the mixture was washed and separated, then, the aqueous layer was discarded, further, washed with saturated saline of double amount of the reaction solvent and the mixture was separated, then, the aqueous layer was discarded. The resultant organic layer was held under reduced pressure and the solvent was distilled off. To the residue was added a mixture of acetonitrile:water=9:1 and the deposited precipitate was filtrated, and suspended and washed with a mixture of acetonitrile:water=9:1, further, suspension washing with acetonitrile was conducted, and the resultant solid was dried under reduced pressure, to obtain a compound 13 (4.70 g, 92.9%).

(Example 21) Synthesis of H-Ser(tBu)-Phe-Arg (Pbf)-Tyr(tBu)-Okb (Compound 14)

The following amino acids were introduced into the compound 13 by repeating a 1 pot condensation de-protection method in which an amine scavenger is added and washing with an ammonium chloride aqueous solution is conducted, to obtain a compound 14.
First residue: Fmoc-Arg(Pbf)-OH
Second residue: Fmoc-Phe-OH
Third residue: Fmoc-Ser(tBu)-OH (Example 22) Synthesis of H-Asn(Trt)-Ser(tBu)-Phe-Arg(Pbf)-Tyr(tBu)-Okb (Compound 15)

The resultant compound 14 (7.58 g, 4.43 mmol) was dissolved in THF so as to give a concentration of 0.05 M, and DIPEA (1.93 ml, 11.1 mmol, 2.5 equiv) was added. Fmoc-Asn(Trt)-OH (3.44 g, 5.76 mmol, 1.3 equiv), COMU (2.28 g, 5.32 mmol, 1.3 equiv) and Oxyma (0.76 g, 5.32 mmol, 1.3 equiv) were dissolved in 8.9 ml of DMF, and DIPEA (1.93 ml, 11.1 mmol, 2.5 equiv) was added and the mixture was stirred at room temperature for 2 minutes. The resultant mixture was added to a THF solution of the compound 14, and the mixture was stirred at room temperature for 10 minutes. As the amine scavenger, propylamine (728 µL, 8.86 mmol, 2 equiv) was added and the mixture was stirred at room temperature for 30 minutes. Piperidine (658 µL, 6.65 mmol, 1.5 equiv) and DBU (4.64 ml, 31.0 mmol, 7 equiv) were added and the mixture was stirred at room temperature for 10 minutes. Concentrated hydrochloric acid was added until pH of the reaction mixture became around 6. A solution of saturated ammonium chloride aqueous solution:water=1:2 of double amount of the reaction solvent was added to the reaction mixture, and the mixture was washed and separated, and the aqueous layer was discarded. Further, a solution of saturated saline:water=1:2 of double amount of the reaction solvent was added, and the mixture was washed and separated, and the aqueous layer was discarded. Further, saturated saline of double amount of the reaction solvent was added, and the mixture was washed and separated, and the aqueous layer was discarded. The resultant organic layer was held under reduced pressure and the solvent was distilled off. To the residue was added a mixture of acetonitrile:water=9:1 and the deposited precipitate was filtrated, further, suspension washing with acetonitrile was conducted, and the resultant solid was dried under reduced pressure, to obtain a compound 15 (8.74 g, 95.4%).

(Example 23) Synthesis of H-Gly-Leu-Gly-Cys (Trt)-Asn(Trt)-Ser(tBu)-Phe-Arg(Pb-Tyr(tBu)-Okb (Compound 16)

The following amino acids were introduced into the resultant compound 15 by repeating a 1 pot condensation de-protection method in which an amine scavenger is added and washing with an ammonium chloride aqueous solution is conducted, to obtain a compound 16.
Sixth residue: Fmoc-Cys(Trt)-OH
Seventh residue: Fmoc-Gly-OH
Eighth residue: Fmoc-Leu-OH
Ninth residue: Fmoc-Gly-OH (Example 24) Synthesis of H-Gln(Trt)-Ser($\psi_{Me, Me}$ Pro)-Gly-Leu-Gly-Cys(Trt)-Asn(Trt)-Ser(tBu)-Phe-Arg(Pbf)-Tyr(tBu)-Okb (Compound 17)

The compound 16 (10.68 g, 4.06 mmol) obtained in Example 23 was dissolved in a mixture of THF:DMF (9/1) so as to give a concentration of 0.05 M, Fmoc-Gln(Trt)-Ser($\psi_{Me, Me}$ Pro)-OH (3.88 g, 5.28 mmol, 1.3 equiv), DMT-MM (1.30 g, 4.59 mmol, 1.13 equiv) and DIPEA (845 µL, 4.87 mmol, 1.2 equiv) were added and the mixture was stirred at room temperature for 30 minutes. As the amine scavenger, propylamine (665 µL, 8.12 mmol, 2 equiv) was added and the mixture was stirred at room temperature for 30 minutes. Piperidine (601 µL, 6.09 mmol, 1.5 equiv) and DBU (6.05 ml, 40.6 mmol, 10 equiv) were added and the mixture was stirred at room temperature for 10 minutes. Concentrated hydrochloric acid was added until pH of the reaction mixture became around 6. A solution of saturated ammonium chloride aqueous solution:water=1:2 of double amount of the reaction solvent was added to the reaction mixture, and the mixture was washed and separated, and the aqueous layer was discarded. Further, a solution of saturated saline:water=1:2 of double amount of the reaction solvent was added, and the mixture was washed and separated, and the aqueous layer was discarded. Further, saturated saline of double amount of the reaction solvent was added, and the liquid was washed and separated, and the aqueous layer was discarded. The resultant organic layer was held under reduced pressure and the solvent was distilled off. To the residue was added water and the deposited precipitate was filtrated, and suspended and washed with n-hexane, and the resultant solid was dried under reduced pressure, to obtain a compound 17 (12.85 g, 100.0%). The resultant compound 17 was analyzed by TLC (n-hexane:ethyl acetate=9:1), but the presence of dibenzofulvene was not observed.

(Example 25) Synthesis of H-D-Arg-Arg-Pro-Hyp-Gly-Thi-Ser-D-Tic-Oic-Arg-OH (Compound 21)

Synthesis of Compound 18

[Chemical Formula 50]

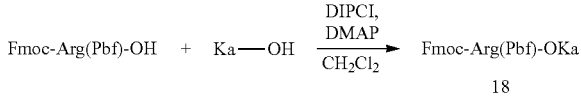

3,4,5-trioctadecyloxybenzyl alcohol (expressed as "Ka-OH") (9.14 g, 10.00 mmol) was dissolved in DCM (100 ml), Fmoc-Arg(Pbf)-OH (9.73 g, 15.00 mmol, 1.5 equiv), DIPCI (2337 µL, 15.00 mmol, 1.5 equiv) and DMAP (61 mg, 0.50 mmol, 0.05 equiv) were added and the mixture was stirred at room temperature for 30 minutes. Propylamine (1644 µL, 20.0 mmol, 2.0 equiv) was added and the mixture was stirred at room temperature for 30 minutes. The precipitate was filtrated, and the filtrate was distilled off under reduced pressure. To the residue was added MeOH and the deposited precipitate was filtrated, suspension washing with MeOH was conducted, further, suspension washing with acetonitrile was conducted, and the resultant solid was dried under reduced pressure, to obtain a compound 18 (15.40 g, 99.7%).

Synthesis of Compound 19

[Chemical Formula 51]

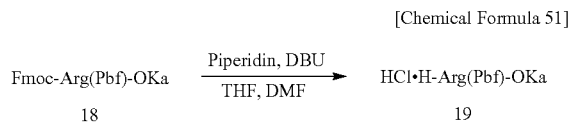

The compound 18 (15.40 g, 10.00 mmol) was dissolved in a mixture of THF (179 ml) and DMF (20 ml), piperidine (1480 µL, 14.9 mmol, 1.5 equiv) and DBU (1490 µL, 9.96 mmol, 1 equiv) were added and the mixture was stirred at room temperature for 10 minutes. Concentrated hydrochloric acid was added until pH of the reaction mixture became around 6. A solution of saturated saline:water=2:1 of double amount of the reaction solvent was added to the reaction mixture and the mixture was washed and separated, then, the aqueous layer was discarded, further, washed with saturated saline of double amount of the reaction solvent and the mixture was separated, then, the aqueous layer was discarded. The resultant organic layer was held under reduced pressure and the solvent was distilled off. To the residue was added acetonitrile and the deposited precipitate was filtrated, and suspended and washed with acetonitrile, and the resultant solid was dried under reduced pressure, to obtain a compound 19 (14.39 g, quant).

Synthesis of Compound 20 (HCl.H-D-Arg(Pbf)-Arg(Pbf)-Pro-Hyp-Gly-Thi-Ser(tBu)-D-Tic-Oic-Arg(Pbf)-OKa)

[Chemical Formula 52]

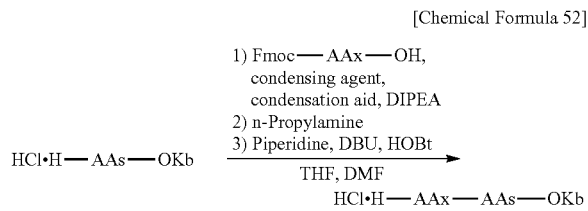

The compound 19 (13.52 g, 9.95 mmol) was subjected to the following method repeatedly, to obtain a compound 20 (24.31 g, 81.6%).

Starting raw materials were dissolved in a mixture of THF:DMF (9/1) so as to give a concentration of 0.05 M, Fmoc-AAx-OH (the equivalent is shown in AA equivalent in the table of the reaction conditions), a condensing agent show in the following table (the equivalent is shown in condensing agent equivalent in the table of the reaction conditions), a condensation aid shown in the following table (the equivalent is shown in condensation aid equivalent in the table of the reaction conditions) and DIPEA (the equivalent is shown in base equivalent in the table of the reaction conditions) were added and the condensation reaction thereof was conducted as shown in the table of the reaction conditions. Next, as the amine scavenger, propylamine (the equivalent is shown in scavenger equivalent in the table of the reaction conditions) was added and the mixture was stirred at room temperature for 30 minutes. Thereafter, HOBt (the equivalent is shown in HOBt equivalent in the table of the reaction conditions), piperidine (1.5 equiv) and DBU (the equivalent is shown in DBU equivalent in the table of the reaction conditions) were added and the mixture was stirred at room temperature for 10 minutes. Next, concentrated hydrochloric acid was added until pH of the reaction mixture became around 6.

The first washing solution shown in the table of the washing conditions was added in double amount of the reaction solvent to the reaction mixture, and the mixture was washed and separated, and the aqueous layer was discarded. If necessary, the second washing solution shown in the table of the washing conditions was added in double amount of the reaction solvent, and the mixture was washed and separated, and the aqueous layer was discarded. Further, saturated saline of double amount of the reaction solvent was added, and the mixture was washed and separated, and the aqueous layer was discarded. The resultant organic layer was held under reduced pressure and the solvent was distilled off. To the residue was added a poor solvent shown in the table of the washing conditions and the deposited precipitate was filtrated, further, a suspension washing solvent shown in the table of the washing conditions was added and suspension washing was conducted, and the resultant solid was dried under reduced pressure, to obtain an amino acid condensate.

TABLE 2

Reaction Consition Table

| | Fmoc-AAx-OH | AA equivalent | condensing agent | condensing agent equivalent | condensation aid |
|---|---|---|---|---|---|
| 2nd residue | Fmoc-Oic-OH | 1.5 | DMT-MM | 1.4 | none |
| 3rd residue | Fmoc-D-Tic-OH | 1.5 | COMU | 1.45 | Oxyma |
| 4th residue | Fmoc-Ser-(tBu)-OH | 1.5 | DMT-MM | 1.4 | none |
| 5th residue | Fmoc-Thi-OH | 1.3 | DMT-MM | 1.2 | none |
| 6th residue | Fmoc-Gly-OH | 1.3 | DMT-MM | 1.2 | none |
| 7th residue | Fmoc-Hyp-OH | 1.3 | DMT-MM | 1.2 | none |
| 8th residue | Fmoc-Pro-OH | 1.5 | DMT-MM | 1.45 | none |

TABLE 2-continued

Reaction Consition Table

| 9th residue | Fmoc-Arg(Pbf)-OH | 1.5 | DMT-MM | 1.45 | none |
| 10th residue | Fmoc-D-Arg(Pbf)-OH | 1.8 | DMT-MM | 1.62 | none |

| | condensation aid equivalent | base equivalent | reaction condition | scavenger equivalent | HOBt equivalent | DBU equivalent |
|---|---|---|---|---|---|---|
| 2nd residue | none | 1.2 | R.T. for 30 min | 3 | 1 | 8 |
| 3rd residue | 1.45 | 4.8 | R.T. for 30 min | 3 | 0 | 7 |
| 4th residue | none | 1.2 | R.T. for 30 min | 3 | 0 | 7 |
| 5th residue | none | 1.2 | R.T. for 30 min | 2 | 0 | 7 |
| 6th residue | none | 1.2 | R.T. for 30 min | 2 | 0 | 7 |
| 7th residue | none | 1.2 | R.T. for 30 min | 2 | 0 | 7 |
| 8th residue | none | 1.2 | R.T. for 30 min | 2 | 0 | 7 |
| 9th residue | none | 1.2 | R.T. for 30 min | 2 | 0 | 7 |
| 10th residue | none | 2.4 | R.T. for 30 min then 40° C. for 30 min | 5 | 0 | 7 |

TABLE 3

Washing Condition Table

| | washing solution (1st) | washing solution (2nd) | poor solvent | suspension-washing solvent |
|---|---|---|---|---|
| 2nd residue | saturated saline:water = 1:2 | none | acetonitrile | acetonitrile |
| 3rd residue | saturated ammonium chloride aqueous solution:water = 1:2 | saturated saline:water = 1:2 | cold water | cold acetonitrile |
| 4th residue | saturated saline:water = 1:2 | none | cold water | cold acetonitrile |
| 5th residue | saturated saline:water = 1:2 | none | acetonitrile:water = 9:1 | acetonitrile |
| 6th residue | saturated saline:water = 1:2 | none | acetonitrile:water = 9:1 | acetonitrile |
| 7th residue | saturated saline:water = 1:2 | none | acetonitrile:water = 9:1 | acetonitrile |
| 8th residue | saturated saline:water = 1:2 | none | cold acetonitrile | cold acetonitrile |
| 9th residue | saturated saline:water = 1:2 | none | cold acetonitrile | cold acetonitrile |
| 10th residue | saturated saline:water = 1:2 | none | acetonitrile | acetonitrile |

Synthesis of Compound 21

[Chemical Formula 53]

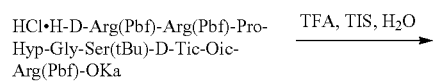

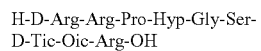

20

The compound 20 (10.0 g, 3.1 mmol) was dissolved in 155 ml of a mixture of TFA:TIS:water=90:2.5:7.5, and the mixture was stirred at room temperature for 4 hours. The reaction mixture was filtrated through Celite. The filtration residue was washed with 30 ml of TFA and filtrated. The resultant filtrates were combined together, and put into 1.85 L of cold isopropyl ether while stirring. The resultant solid was filtrated, and the filtration residue was further suspended and washed with cold isopropyl ether and filtrated, twice. The resultant solid was dried, to obtain a compound 21 (5.17 g, Quant, HPLC purity 77.36%). The resultant compound was measured by LC-MS, to observe 652.9 [M+2H$^+$]/2.

(Example 26) Synthesis of H-Ala-Gln(Trt)-Ser($\psi_{Me,Me}$Pro)-Gly-Leu-Gly-Cys(Trt)-Asn(Trt)-Ser(tBu)-Phe-Arg(Pbf)-Tyr(t Bu)-OKb (Compound 22)

Fmoc-Ala-OH was introduced into the compound 17 obtained in Example 24 by a 1 pot condensation de-protection method in which an amine scavenger is added and washing with an ammonium chloride aqueous solution is conducted, to obtain a compound 22 (12.42 g, Quant).

(Example 27) Synthesis of Fmoc-Ser(tBu)-Leu-Arg(Pbf)-Arg(Pbf)-Ser(tBu)-Ser(tBu)-Cys(Trt)-Phe-Gly-OH (Compound 26)

Synthesis of Compound 23 (HCl.H-Gly-OKb)

Fmoc-Gly-OH was used in the same manner as in Example 17 on Kb-OH (7.57 g, 10.0 mmol), to obtain a compound 23 (7.90 g, 93.1%).

Synthesis of Compound 24 (HCl.H-Leu-Arg(Pbf)-Arg(Pbf)-Ser(tBu)-Ser(tBu)-Cys(Trt)-Phe-Gly-OKb)

[Chemical Formula 54]

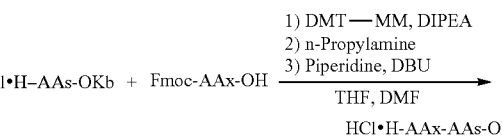

Introduction of
Second residue: Fmoc-Phe-OH
Third residue: Fmoc-Cys(Trt)-OH
Fourth residue: Fmoc-Ser(tBu)-OH
Fifth residue: Fmoc-Ser(tBu)-OH
Sixth residue: Fmoc-Arg(Pbf)-OH
Seventh residue: Fmoc-Arg(Pbf)-OH
Eighth residue: Fmoc-Leu-OH Amino acids were introduced sequentially into the compound 23 (7.89 g, 9.25 mmol) by repeating the following method, to obtain a compound 24 (20.27 g, 85.5%).

Starting raw materials were processed using a 1 pot condensation de-protection method in which an amine scavenger is added and washing with an ammonium chloride aqueous solution is conducted (here, Fmoc-amino acid (1.3 equiv) and DMT-MM (1.13 equiv) are used, washing with an ammonium chloride aqueous solution is omitted), to obtain an amino acid condensate.

Synthesis of Compound 25 (Fmoc-Ser(tBu)-Leu-Arg(Pbf)-Arg(Pbf)-Ser(tBu)-Ser(tBu)-Cys(Trt)-Phe-Gly-OKb)

Fmoc-Ser(tBu)-OH was introduced into the compound 24 (20.26 g, 7.91 mmol) by an amino acid condensation general synthesis method, to obtain a compound 25 (22.56 g, Quant).

Synthesis of Compound 26 (Fmoc-Ser(tBu)-Leu-Arg(Pbf)-Arg(Pbf)-Ser(tBu)-Ser(tBu)-Cys(Trt)-Phe-Gly-OH)

A Kb protective group general de-protection method was applied on the compound 25 (22.56 g, 7.80 mmol), to obtain a compound 26 (22.56 g, Quant).

(Example 28) Synthesis of HCl.H-Ser(tBu)-Leu-Arg(Pbf)-Arg(Pbf)-Ser(tBu)-Ser(tBu)-Cys(Trt)-Phe-Gly-Gly-Arg(Pbf)-Met-Asp(OtBu)-Arg(Pbf)-Ile-Gly-Ala-Gln(Trt)-Ser($\psi_{Me,Me}$ Pro)-Gly-Leu-Gly-Cys(Trt)-Asn(Trt)-Ser(tBu)-Phe-Arg(Pbf)-Tyr(tBu)-OKb (Compound 28)

Synthesis of Compound 27 (HCl.H-Gly-Arg(Pbf)-Met-Asp(OtBu)-Arg(Pbf)-Ile-Gly-Ala-Gln(Trt)-Ser($\psi_{Me,Me}$ Pro)-Gly-Leu-Gly-Cys(Trt)-Asn(Trt)-Ser(tBu)-Phe-Arg(Pbf)-Tyr(tBu)-OKb)

The compound 11 (11.33 g, 5.8 mmol, 1.5 equiv) obtained in Example 19 was dissolved in DMF (38.7 ml), and THF (348 ml) was added for dilution, and the compound 22 (12.42 g, 3.87 mmol, 1.0 equiv) obtained in Example 26, HATU (1.99 g, 5.22 mmol, 1.35 equiv), HOAt (711 mg, 5.22 mmol, 1.35 equiv) and DIPEA (3369 μL, 19.3 mmol, 5.0 equiv) were added, and the mixture was stirred at room temperature for 30 minutes. As the amine scavenger, propylamine (318 μL, 3.87 mmol, 1 equiv) was added and the mixture was stirred at room temperature for 30 minutes. Further, piperidine (575 μL, 5.80 mmol, 1.0 equiv) and DBU (5.79 ml, 38.7 mmol, 10 equiv) were added and the mixture was stirred at room temperature for 10 minutes. Concentrated hydrochloric acid was added until pH of the reaction mixture became around 6. A solution of saturated ammonium chloride aqueous solution:water=1:2 of double amount of the reaction solvent was added to the reaction mixture, and the mixture was washed and separated, and the aqueous layer was discarded. Further, a solution of saturated saline:water=1:2 of double amount of the reaction solvent was added, and the mixture was washed and separated, and the aqueous layer was discarded. Further, saturated saline of double amount of the reaction solvent was added, and the liquid was washed and separated, and the aqueous layer was discarded. The resultant organic layer was held under reduced pressure and the solvent was distilled off. To the residue was added a mixture of acetonitrile:water=9:1 and the deposited precipitate was filtrated, and suspended and washed with acetonitrile, and the resultant solid was dried under reduced pressure, to obtain a compound 27 (15.29 g, quant).

Synthesis of Compound 28 (HCl.H-Ser(tBu)-Leu-Arg(Pbf)-Arg(Pbf)-Ser(tBu)-Ser(tBu)-Cys(Trt)-Phe-Gly-Gly-Arg(Pbf)-Met-Asp(OtBu)-Arg(Pbf)-Ile-Gly-Ala-Gln(Trt)-Ser($\psi_{Me,Me}$ Pro)-Gly-Leu-Gly-Cys(Trt)-Asn(Trt)-Ser(tBu)-Phe-Arg(Pbf)-Tyr(tBu)-OKb)

[Chemical Formula 55]

HCl•H-Ala-Gln(Trt)-Ser(ψMe, Me Pro)-Gly-Leu-Gyl-Cys(Trt)-Asn(Trt)-Ser(tBu)-Phe-Arg(Pbf)-Tyr(tBu)-OKb

22

1) Fmoc-Gly-Arg(Pbf)-Met-Asp(OtBu)-Arg(Pbf)-Ile-Gly-OH.

11

HATU, HOAt, DIPEA
2) n-Propylamine
3) Piperidine, DBU

THF, DMF
⟶

HCl•H-Gly-Arg(Pbf)-Met-Asp(OtBu)-Arg(Pbf)-Ile-Gly-Ala-Gln(Trt)-Ser(ψMe, Me Pro)-Gly-Leu-Gyl-Cys(Trt)-Asn(Trt)-Ser(tBu)-Phe-Arg(Pbf)-Tyr(tBu)-Okb

27

[Chemical Formula 56]

HCl•H-Arg(Pbf)-Met-Asp(OtBu)-Arg(Pbf)-Ile-Gly-Ala-Gln(Trt)-Ser(ψMe, Me Pro)-Gly-Leu-Gyl-Cys(Trt)-Asn(Trt)-Ser(tBu)-Phe-Arg(Pbf)-Tyr(tBu)-OKb

27

1) Fmoc-Ser(tBu)-Leu-Arg(Pbf)-Arg(Pbf)-Ser(tBu)-Ser(tBu)-Cys(Trt)-Phe-Gly-OH.

26

HATU, HOAt, DIPEA
2) n-Propylamine
3) Piperidine, DBU

THF, DMF
⟶

-continued

HCl•H-Ser(tBu)-Leu-Arg(Pbf)-
Arg(Pbf)-Ser(tBu)-Ser(tBu)-
Cys(Trt)-Phe-Gly-Gly-Arg(Pbf)-
Met-Asp(OtBu)-Arg(Pbf)-Ile-
Gly-Ala-Gln(Trt)-
Ser(ψMe, Me Pro)-Gly-
Leu-Gyl-Cys(Trt)-Asn(Trt)-
Ser(tBu)-Phe-Arg(Pbf)-
Tyr(tBu)-Okb

28

On the compound 27 (17.63 g, 3.87 mmol), the compound 26 (12.47 g, 5.80 mmol, 1.5 equiv) obtained in Example 27 was used and reacted in the same manner as for synthesis of the compound 27, to obtain a compound 28 (26.83 g, quant).

(Example 29) Synthesis of H-Ser-Leu-Arg-Arg-Ser-Ser-Ser-Phe-Gly-Gly-Arg-Met-Asp-Arg-Ile-Gly-Gln-Ser-Gly-Leu-Gly-Cys-Asn-Ser-Phe-Arg-Tyr-OH (7Cys-23Cys, SS Bond) (Compound 30)

Synthesis of Compound 29 (H-Ser-Leu-Arg-Arg-Ser-Ser-Ser-Phe-Gly-Gly-Arg-Met-Asp-Arg-Ile-Gly-Gln-Ser-Gly-Leu-Gly-Cys-Asn-Ser-Phe-Arg-Tyr-OH)

[Chemical Formula 57]

HCl•H-Ser(tBu)-Leu-Arg(Pbf)-
Arg(Pbf)-Ser(tBu)-Ser(tBu)-
Cys(Trt)-Phe-Gly-Gly-Arg(Pbf)-
Met-Asp(OtBu)-Arg(Pbf)-Ile-
Gly-Ala-Gln(Trt)-             TFA, TIS, H₂O, EDT
Ser(ψMe, Me Pro)-Gly-         ────────────────▶
Leu-Gyl-Cys(Trt)-Asn(Trt)-
Ser(tBu)-Phe-Arg(Pbf)-
Tyr(tBu)-OKb

28

H-Ser-Leu-Arg-Arg-Ser-Ser-
Cys-Phe-Gly-Gly-Arg-Met-
Asp-Arg-Ile-Gly-Ala-Gln-
Ser-Gly-Leu-Gyl-Cys-Asn-
Ser-Phe-Arg-Tyr-OH

29

The compound 28 (6.93 g, 1.0 mmol) was dissolved in 200 ml of a mixture of TFA:TIS:water:EDT=80:5:10:5, and the mixture was stirred at room temperature for 4 hours. The reaction liquid was filtrated through Celite, and the filtration residue was washed with 100 ml of TFA and filtrated. The resultant filtrates were combined together, and put into 3.0 L of cold isopropyl ether while stirring. The resultant solid was filtrated, and the filtration residue was further suspended and washed with cold isopropyl ether and filtrated, twice. The resultant solid was dried, to obtain a compound 29 (3.90 g, Quant, HPLC purity 55.22%).

Synthesis of Compound 30 (H-Ser-Leu-Arg-Arg-Ser-Ser-Ser-Phe-Gly-Gly-Arg-Met-Asp-Arg-Ile-Gly-Gln-Ser-Gly-Leu-Gly-Cys-Asn-Ser-Phe-Arg-Tyr-OH (7 Cys-23Cys, SS Bond))

[Chemical Formula 58]

H-Ser-Leu-Arg-Arg-Ser-Ser-
Cys-Phe-Gly-Gly-Arg-Met-        Air
Asp-Arg-Ile-Gly-Ala-Gln-      ──────▶
Ser-Gly-Leu-Gyl-Cys-Asn-        H₂O
Ser-Phe-Arg-Tyr-OH

29

H-Ser-Leu-Arg-Arg-Ser-Ser-
Cys-Phe-Gly-Gly-Arg-Met-Asp-Arg-Ile-
                                  |
                                  |
Gly-Ala-Gln-Ser-Gly-Leu-Gyl-Cys-Asn-
Ser-Phe-Arg-Tyr-OH

30

The compound 29 (3.90 g, 1.0 mmol) was dissolved in 3.77 L of water, and the solution was adjusted to pH7.1 with pyridine, and stirred overnight. The resultant reaction mixture was freeze-dried, to obtain a compound 30 (3.47 g, 92.2%, HPLC purity 65.07%). The resultant compound was measured by LC-MS, to observe 1027.2 [M+3H⁺]/3.

(Example 30) Synthesis of H-Glu(OtBu)-Ile-Pro-Glu(OtBu)-Glu(OtBu)-Tyr(tBu)-Leu-OKb (Compound 33)

Synthesis of Compound 31

[Chemical Formula 59]

Fmoc-Leu-OH + Kb—OH  $\xrightarrow{\text{DIPCI, DMAP}}_{CH_2Cl_2}$  Fmoc-Leu-OKb

31

Fmoc-Leu-OH was used in the same manner as in Example 18 on Kb-OH (2.27 g, 3.00 mmol), to obtain a compound 31 (3.26 g, 99.6%).

Synthesis of Compound 32

[Chemical Formula 60]

Fmoc-Leu-OKb  $\xrightarrow{\text{Poiperidin, DBU}}_{\text{THF, DMF}}$  HCl•H-Leu-OKb 31                                                32

A de-Fmoc general synthesis method was applied on the compound 31 (3.26 g, 2.98 mmol), to obtain a compound 32 (2.72 g, Quant).

Synthesis of Compound 33 (H-Glu(OtBu)-Ile-Pro-Glu(OtBu)-Glu(OtBu)-Tyr(tBu)-Leu-OKb)

(Example 31) Synthesis of Fmoc-Gly-Gly-Asn(Trt)-Gly-Asp(OtBu)-Phe-Glu(OtBu)-OH (Compound 38)

Synthesis of Compound 34

[Chemical Formula 61]

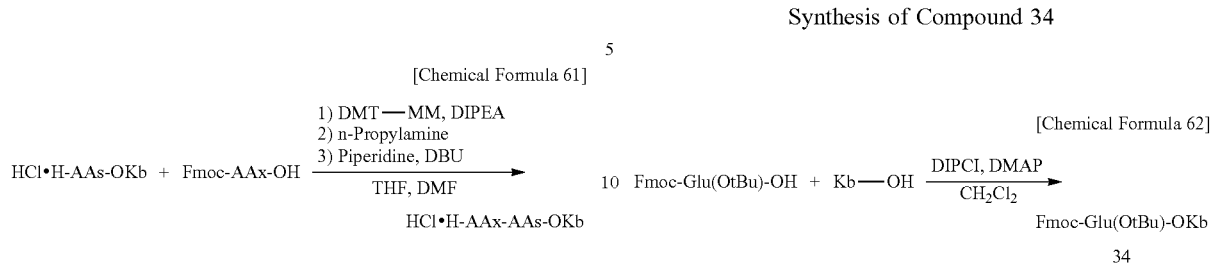

Introduction of
Second residue: Fmoc-Tyr(tBu)-OH
Third residue: Fmoc-Glu(OtBu)-OH
Fourth residue: Fmoc-Glu(OtBu)-OH
Fifth residue: Fmoc-Pro-OH
Sixth residue: Fmoc-Ile-OH
Seventh residue: Fmoc-Glu(OtBu)-OH Amino acids were introduced sequentially into the compound 32 (2.70 g, 2.98 mmol) by repeating the following method, to obtain a compound 33 (4.40 g, 77.7%).

Starting raw materials were dissolved in a mixture of THF:DMF (9/1) so as to give a concentration of 0.05 M, Fmoc-amino acid (1.3 equiv), DMT-MM (1.2 equiv) and DIPEA (1.2 equiv) were added and the mixture was stirred at room temperature for 30 minutes. As the amine scavenger, propylamine (2 equiv) was added and the mixture was stirred at room temperature for 30 minutes. HOBt (1 equiv) (only second residue), piperidine (1.5 equiv) and DBU (7 equiv, for only second residue: 8 equiv) were added and the mixture was stirred at room temperature for 10 minutes. Concentrated hydrochloric acid was added until pH of the reaction mixture became around 6. A solution of saturated saline:water=1:2 of double amount of the reaction solvent was added to the reaction mixture, and the mixture was washed and separated, and the aqueous layer was discarded. Further, saturated saline of double amount of the reaction solvent was added, and the mixture was washed and separated, and the aqueous layer was discarded. The resultant organic layer was held under reduced pressure and the solvent was distilled off. To the residue was added acetonitrile and the deposited precipitate was filtrated, and suspended and washed with acetonitrile, and the resultant solid was dried under reduced pressure, to obtain an amino acid condensate.

[Chemical Formula 62]

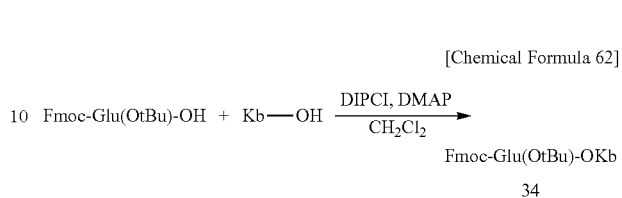

Fmoc-Glu(OtBu)-OH was used in the same manner as in Example 18 on Kb-OH (3.41 g, 4.50 mmol), to obtain a compound 34 (5.05 g, 96.3%).

Synthesis of Compound 35

[Chemical Formula 63]

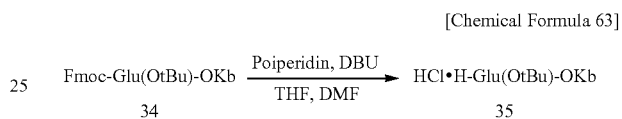

A de-Fmoc general synthesis method was applied on the compound 34 (5.04 g, 4.33 mmol), to obtain a compound 35 (4.24 g, Quant).

Synthesis of Compound 36 (HCl.H-Gly-Asn(Trt)-Gly-Asp(OtBu)-Phe-Glu(OtBu)-OKb)

[Chemical Formula 64]

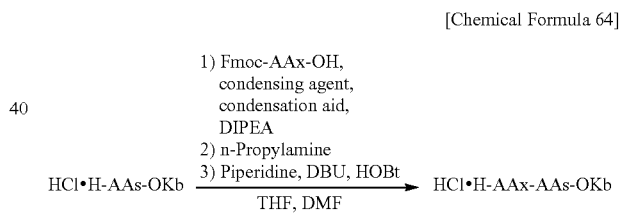

The compound 35 (4.23 g, 4.33 mmol) was processed by the same manner as for synthesis of the compound 20, according to the table of the reaction conditions and the table of the washing conditions shown below, to obtain a compound 36 (7.05 g, 90.8%).

TABLE 4

Reaction Condition Table

| | Fmoc-AAx-OH | AA equivalent | condensing agent | condensing agent equivalent | condensation aid |
|---|---|---|---|---|---|
| 2nd residue | Fmoc-Phe-OH | 1.3 | DMT-MM | 1.2 | none |
| 3rd residue | Fmoc-Asp(OtBu)-OH | 1.3 | DMT-MM | 1.2 | none |
| 4th residue | Fmoc-Gly-OH | 1.3 | DMT-MM | 1.2 | none |
| 5th residue | Fmoc-Asn(Trt)-OH | 1.3 | DMT-MM | 1.2 | none |
| 6th residue | Fmoc-Gly-OH | 1.95 | DMT-MM | 1.8 | none |

TABLE 4-continued

Reaction Condition Table

| | condensation aid equivalent | base equivalent | reaction condition | scavenger equivalent | HOBt equivalent | DBU equivalent |
|---|---|---|---|---|---|---|
| 2nd residue | none | 1.2 | R.T. for 30 min | 2 | 1 | 8 |
| 3rd residue | none | 1.2 | R.T. for 30 min | 2 | 0 | 7 |
| 4th residue | none | 1.2 | R.T. for 30 min | 2 | 0 | 7 |
| 5th residue | none | 1.2 | R.T. for 30 min | 2 | 0 | 7 |
| 6th residue | none | 1.75 | R.T. for 30 min | 2 | 0 | 7 |

TABLE 5

Washing Condition Table

| | washing solution (1st) | washing solution (2nd) | poor solvent | suspension-washing solvent |
|---|---|---|---|---|
| 2nd residue | saturated saline:water = 1:2 | none | acetonitrile | acetonitrile |
| 3rd residue | saturated saline:water = 1:2 | none | acetonitrile | acetonitrile |
| 4th residue | saturated saline:water = 1:2 | none | acetonitrile | acetonitrile |
| 5th residue | saturated saline:water = 1:2 | none | acetonitrile | acetonitrile |
| 6th residue | saturated saline:water = 1:2 | none | acetonitrile | acetonitrile |

Synthesis of Compound 37

[Chemical Formula 65]

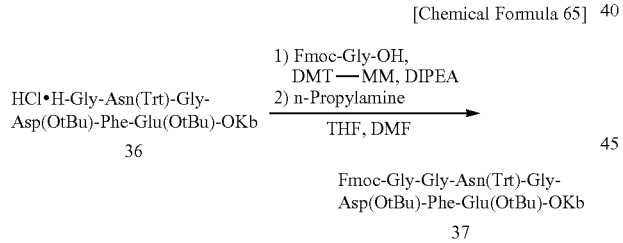

The compound 36 (7.04 g, 3.90 mmol) was dissolved in a mixture of THF (65 ml) and DMF (7.2 ml), Fmoc-Gly-OH (1.39 g, 4.68 mmol, 1.2 equiv), DMT-MM (1.20 g, 4.32 mmol, 1.11 equiv) and DIPEA (753 μL, 4.32 mmol, 1.11 equiv) were added and the mixture was stirred at room temperature for 30 minutes. As the amine scavenger, propylamine (888 μL, 10.8 mmol, 2.77 equiv) was added and the mixture was stirred at room temperature for 30 minutes. The resultant organic layer was held under reduced pressure and the solvent was distilled off. To the residue was added a solution of acetonitrile:water=9:1 and the solution was cooled, and the deposited precipitate was filtrated, and suspended and washed with acetonitrile, further, suspension washing with acetonitrile was conducted, and the resultant solid was dried under reduced pressure, to obtain a compound 37 (7.16 g, 90.4%).

Synthesis of Compound 38 (Fmoc-Gly-Gly-Asn(Trt)-Gly-Asp(OtBu)-Phe-Glu(OtBu)-OH)

A Kb protective group general de-protection method was applied on the compound 37 (2.20 g, 1.09 mmol), to obtain a compound 38 (1.21 g, 83.0%).

(Example 32) Synthesis of Fmoc-D-Phe-Pro-Arg(Pbf)-Pro-Gly-Gly-OH (Compound 42)

Synthesis of Compound 39 (HCl.H-Gly-OKb)

Fmoc-Gly-OH was used in the same manner as in Example 17 on Kb-OH (3.41 g, 4.5 mmol), to obtain a compound 39 (3.58 g, 90.2%).

Synthesis of Compound 40
(HCl.H-Pro-Arg(Pbf)-Pro-Gly-Gly-OKb)

[Chemical Formula 66]

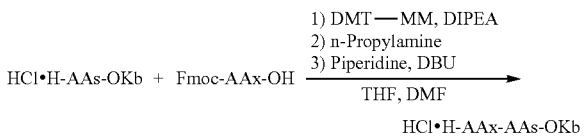

Introduction of
Second residue: Fmoc-Gly-OH
Third residue: Fmoc-Pro-OH
Fourth residue: Fmoc-Arg(Pbf)-OH
Fifth residue: Fmoc-Pro-OH
Amino acids were introduced sequentially into the compound 39 (3.33 g, 3.91 mmol) by repeating the following method, to obtain a compound 40 (5.11 g, 85.7%).

Starting raw materials were dissolved in a mixture liquid of THF:DMF (9/1) so as to give a concentration of 0.05 M, Fmoc-amino acid (1.3 equiv), DMT-MM (1.2 equiv) and DIPEA (1.2 equiv) were added and the mixture was stirred at room temperature for 30 minutes. As the amine scavenger, propylamine (2 equiv) was added and the mixture was stirred at room temperature for 30 minutes. HOBt (1 equiv), piperidine (1.5 equiv) and DBU (7 equiv, only for second residue: 8 equiv) were added and the mixture was stirred at room temperature for 10 minutes. Concentrated hydrochloric acid was added until pH of the reaction mixture became around 6. A solution of saturated saline:water=1:2 of double amount of the reaction solvent was added to the reaction mixture, and the mixture was washed and separated, and the aqueous layer was discarded. Further, saturated saline of double amount of the reaction solvent was added, and the mixture was washed and separated, and the aqueous layer was discarded. The resultant organic layer was held under reduced pressure and the solvent was distilled off. To the residue was added acetonitrile and the deposited precipitate was filtrated, and suspended and washed with acetonitrile, and the resultant solid was dried under reduced pressure, to obtain an amino acid condensate.

Synthesis of Compound 41

[Chemical Formula 67]

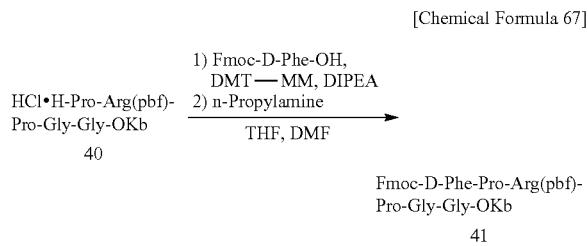

The compound 40 (5.10 g, 3.38 mmol) was dissolved in a mixture of THF (61 ml) and DMF (6.7 ml), Fmoc-D-Phe-OH (1.70 g, 4.39 mmol, 1.3 equiv), DMT-MM (1.12 g, 4.05 mmol, 1.2 equiv) and DIPEA (705 μL, 4.05 mmol, 1.2 equiv) were added and the mixture was stirred at room temperature for 30 minutes. As the amine scavenger, propylamine (555 μL, 6.75 mmol, 2 equiv) was added and the mixture was stirred at room temperature for 30 minutes. The resultant organic layer was held under reduced pressure and the solvent was distilled off. To the residue was added a solution of acetonitrile:water=9:1 and the solution was cooled, and the deposited precipitate was filtrated, and suspended and washed with acetonitrile, further, suspension washing with acetonitrile was conducted, and the resultant solid was dried under reduced pressure, to obtain a compound 41 (5.92 g, 95.2%).

Synthesis of Compound 42 (Fmoc-D-Phe-Pro-Arg(Pbf)-Pro-Gly-Gly-OH)

A Kb protective group general de-protection method was applied on the compound 41 (1.84 g, 1.0 mmol), to obtain a compound 42 (0.942 g, 85.3%).

(Example 33) Synthesis of H-D-Phe-Pro-Arg(Pbf)-Pro-Gly-Gly-Gly-Gly-Asn(Trt)-Gly-Asp(OtBu)-Phe-Glu(OtBu)-Glu(OtBu)-Ile-Pro-Glu(OtBu)-Glu(OtBu)-Tyr(tBu)-Leu-OKb (Compound 44)

Synthesis of Compound 43 (HCl.H-Gly-Gly-Asn(Trt)-Gly-Asp(OtBu)-Phe-Glu(OtBu)-Glu(OtBu)-Ile-Pro-Glu(OtBu)-Glu(OtBu)-Tyr(tBu)-Leu-OKb)

[Chemical Formula 68]

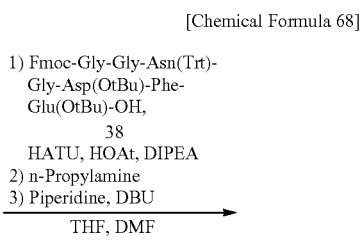
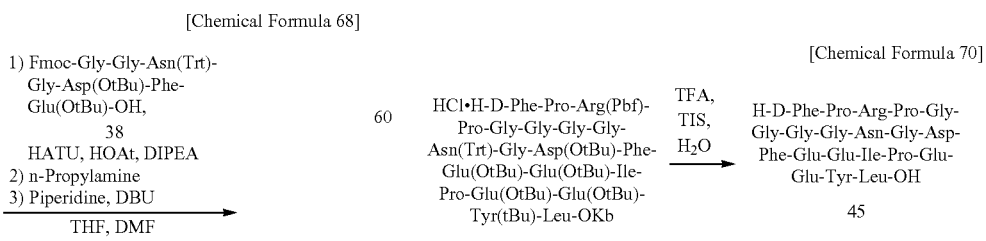

On the compound 33 (568 mg, 0.3 mmol) obtained in Example 30, the compound 38 (573 mg, 0.45 mmol, 1.5 equiv) obtained in Example 31 was used and reacted in the same manner as for synthesis of the compound 27, and liquid-liquid washed, and to the concentrated residue was added a mixture of acetonitrile:water=9:1 and the deposited precipitate was centrifugally separated, and suspended and washed with methanol, further, suspension washing with acetonitrile was conducted, and the resultant solid was dried under reduced pressure, to obtain a compound 43 (725 mg, 82.6%).

Synthesis of Compound 44 (HCl.H-D-Phe-Pro-Arg(Pbf)-Pro-Gly-Gly-Gly-Gly-Asn(Trt)-Gly-Asp(OtBu)-Phe-Glu(OtBu)-Glu(OtBu)-Ile-Pro-Glu(OtBu)-Glu(OtBu)-Tyr(tBu)-Leu-OKb)

[Chemical Formula 69]

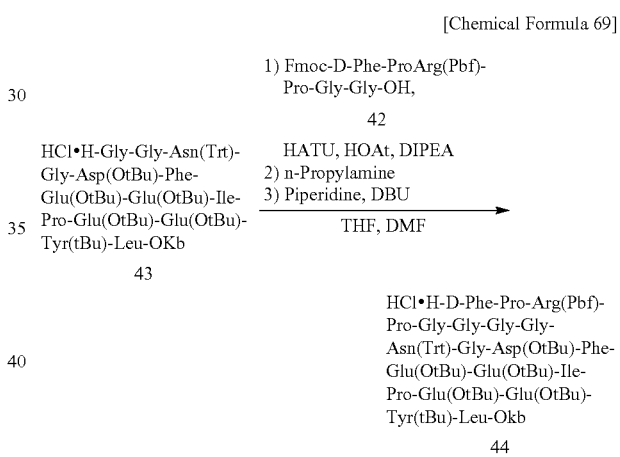

On the compound 43 (715 mg, 0.245 mmol), the compound 42 (405 mg, 0.33 mmol, 1.5 equiv) obtained in Example 32 was used and operated in the same manner as for synthesis of the compound 32, to obtain a compound 44 (863 mg, 93.2%).

(Example 34) Synthesis of H-D-Phe-Pro-Arg-Pro-Gly-Gly-Gly-Gly-Asn-Gly-Asp-Phe-Glu-Glu-Ile-Pro-Glu-Glu-Tyr-Leu-OH (Compound 45)

[Chemical Formula 70]

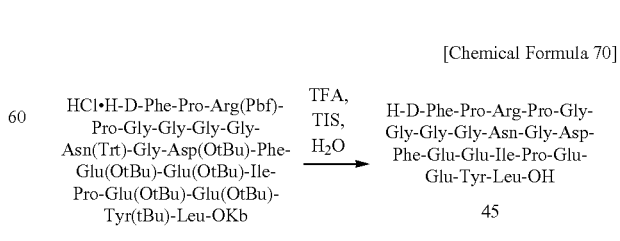

The compound 44 (300 mg, 0.079 mmol) was dissolved in 8 ml of a mixture of TFA:TIS:water=95:2.5:2.5, and the mixture was stirred at room temperature for 3 hours. The reaction mixture was filtrated through Celite. The filtration residue was washed with 3 ml of TFA and filtrated. The resultant filtrates were combined together, and put into 120 mL of cold isopropyl ether while stirring. The resultant solid was centrifugally separated, and the filtration residue was further suspended and washed with cold isopropyl ether and centrifugally separated, four times. The resultant solid was dried, to obtain a compound 45 (147.7 mg, 77.4%, HPLC purity 74.49%).

(Example 35) Synthesis of H-Lys(Boc)-Pro-Pro-Ala-Lys(Boc)-Leu-Gln(Trt)-Pro-Arg(Pbf)-OKb (Compound 50)

Synthesis of Compound 46

[Chemical Formula 71]

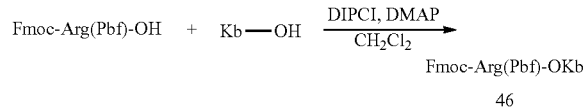

On Kb-OH (2.27 g, 3.0 mmol), Fmoc-Arg(Pbf)-OH (2.92 g, 4.5 mmol, 1.5 equiv) was used in the same manner as in Example 17, to obtain a compound 46 (4.20 g, Quant).

Synthesis of Compound 47

[Chemical Formula 72]

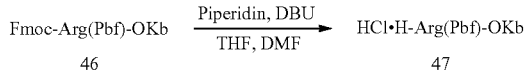

A de-Fmoc general synthesis method was applied on the compound 46 (4.15 g, 2.99 mmol), to obtain a compound 47 (3.51 g, 97.6%).

Synthesis of Compound 48

[Chemical Formula 73]

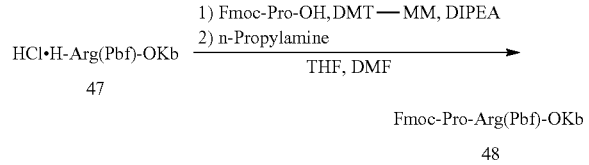

The compound 47 (3.5 g, 2.91 mmol) was dissolved in a mixture of THF (52 ml) and DMF (5.8 ml), Fmoc-Pro-OH (1.28 g, 3.78 mmol, 1.3 equiv), DMT-MM (943 mg, 3.41 mmol, 1.17 equiv) and DIPEA (913 µL, 5.24 mmol, 1.8 equiv) were added and the mixture was stirred at room temperature for 30 minutes. As the amine scavenger, propylamine (479 µL, 5.82 mmol, 2 equiv) was added and the mixture was stirred at room temperature for 30 minutes. The resultant reaction mixture was held under reduced pressure and the solvent was distilled off. To the residue was added acetonitrile and the deposited precipitate was filtrated, and suspended and washed with acetonitrile, and the resultant solid was dried under reduced pressure, to obtain a compound 48 (4.24 g, 98.0%).

Synthesis of Compound 49

[Chemical Formula 74]

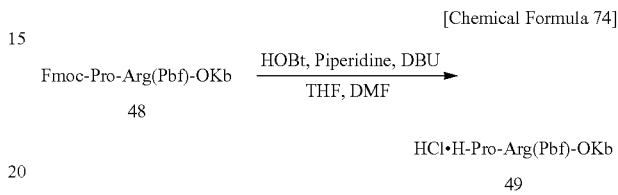

The compound 48 (4.23 g, 2.85 mmol) was dissolved in a mixture liquid of THF (51 ml) and DMF (6 ml), HOBt (388 mg, 2.85 mmol, 1.0 equiv), piperidine (423 µL, 4.27 mmol, 1.5 equiv) and DBU (852 µL, 5.69 mmol, 2 equiv) were added and the mixture was stirred at room temperature for 10 minutes. Concentrated hydrochloric acid was added until pH of the reaction mixture became around 6. A solution of saturated ammonium chloride aqueous solution:water=1:2 of double amount of the reaction solvent was added to the reaction mixture, and the mixture was washed and separated, and the aqueous layer was discarded. Further, a solution of saturated saline:water=1:2 of double amount of the reaction solvent was added, and the mixture was washed and separated, and the aqueous layer was discarded. Further, saturated saline of double amount of the reaction solvent was added, and the mixture was washed and separated, and the aqueous layer was discarded, and the solvent was distilled off under reduced pressure. To the residue was added acetonitrile and the deposited precipitate was filtrated, further, suspended and washed with acetonitrile, and the resultant solid was dried under reduced pressure, to obtain a compound 49 (3.75 g, Quant).

Synthesis of Compound 50 (H-Lys(Boc)-Pro-Pro-Ala-Lys(Boc)-Leu-Gln(Trt)-Pro-Arg(Pbf)-OKb)

[Chemical Formula 75]

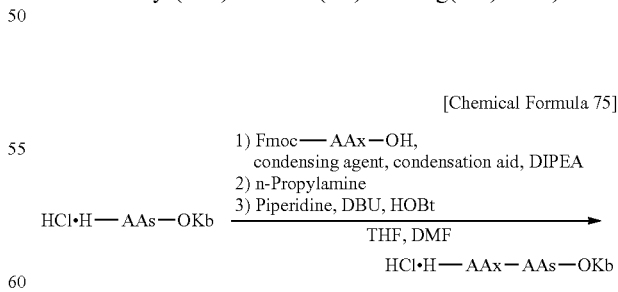

The compound 49 (3.69 g, 2.84 mmol) was processed in the same manner as for synthesis of the compound 20, according to the reaction conditions and the washing conditions shown in the tables below, to obtain a compound 50 (6.02 g, 79.9%).

TABLE 6

Reaction Consition Table

| | Fmoc-AAx-OH | AA equivalent | condensing agent | condensing agent equivalent | condensation aid |
|---|---|---|---|---|---|
| 3rd residue | Fmoc-Glu(Trt)-OH | 1.5 | DMT-MM | 1.4 | none |
| 4th residue | Fmoc-Leu-OH | 1.95 | DMT-MM | 1.76 | none |
| 5th residue | Fmoc-Lys(Boc)-OH | 1.3 | DMT-MM | 1.17 | none |
| 6th residue | Fmoc-Ala-OH | 1.3 | DMT-MM | 1.2 | none |
| 7th residue | Fmoc-Pro-OH | 1.3 | DMT-MM | 1.2 | none |
| 8th residue | Fmoc-Pro-OH | 1.3 | DMT-MM | 1.2 | none |
| 9th residue | Fmoc-Arg(Pbf)-OH | 1.5 | DMT-MM | 1.46 | none |

| | condensation aid equivalent | base equivalent | reaction condition | scavenger equivalent | HOBt equivalent | DBU equivalent |
|---|---|---|---|---|---|---|
| 3rd residue | none | 1.4 | R.T. for 30 min | 3 | 0 | 7 |
| 4th residue | none | 2.4 | R.T. for 30 min | 6 | 0 | 7 |
| 5th residue | none | 1.2 | R.T. for 30 min | 2 | 0 | 10 |
| 6th residue | none | 1.2 | R.T. for 30 min | 2 | 0 | 7 |
| 7th residue | none | 1.2 | R.T. for 30 min | 2 | 0 | 7 |
| 8th residue | none | 1.2 | R.T. for 30 min | 2 | 0 | 7 |
| 9th residue | none | 1.2 | R.T. for 30 min | 2 | 0 | 7 |

TABLE 7

Washing Condition Table

| | washing solution (1st) | washing solution (2nd) | poor solvent | suspension-washing solvent |
|---|---|---|---|---|
| 3rd residue | saturated ammonium chloride aqueous solution: water = 1:2 | saturated saline: water = 1:2 | cold water | cold acetonitrile |
| 4th residue | saturated ammonium chloride aqueous solution: water = 1:2 | saturated saline: water = 1:2 | cold water | cold acetonitrile |
| 5th residue | saturated ammonium chloride aqueous solution: water = 1:2 | saturated saline: water = 1:2 | cold water | cold acetonitrile |
| 6th residue | saturated ammonium chloride aqueous solution: water = 1:2 | saturated saline: water = 1:2 | acetonitrile | acetonitrile |
| 7th residue | saturated ammonium chloride aqueous solution: water = 1:2 | saturated saline: water = 1:2 | acetonitrile | acetonitrile |
| 8th residue | saturated ammonium chloride aqueous solution: water = 1:2 | saturated saline: water = 1:2 | acetonitrile | acetonitrile |
| 9th residue | saturated ammonium chloride aqueous solution: water = 1:2 | saturated saline: water = 1:2 | acetonitrile | acetonitrile |

(Example 36) Synthesis of Fmoc-Lys(Boc)-Leu-Gln(Trt)-Gln(Trt)-Arg(pbf)-Lys(Boc)-Glu(OtBu)-Ser(tBu)-Lys(Boc)-OH (Compound 55)

Synthesis of Compound 51

[Chemical Formula 76]

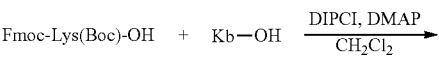

Fmoc-Lys(Boc)-OKb
51

On Kb-OH (1.52 g, 2.0 mmol), Fmoc-Lys(Boc)-OH was used in the same manner as in Example 18, to obtain a compound 51 (2.48 g, Quant).

Synthesis of Compound 52

[Chemical Formula 77]

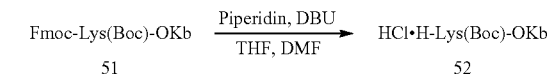

A de-Fmoc general synthesis method was applied on the compound 51 (2.41 g, 1.99 mmol), to obtain a compound 52 (2.01 g, 98.9%).

Synthesis of Compound 53 (HCl.H-Leu-Gln(Trt)-Gln(Trt)-Arg(Pbf)-Lys(Boc)-Glu(OtBu)-Ser(tBu)-Lys(Boc)-OKb)

[Chemical Formula 78]

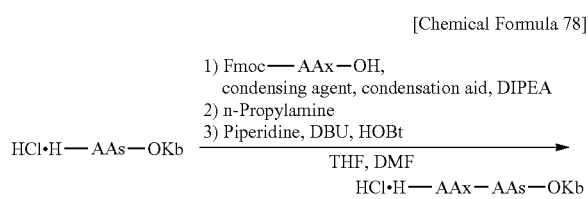

The compound 52 (2.01 g, 1.96 mmol) was processed in the same manner as for synthesis of the compound 20, according to the table of the reaction conditions and the table of the washing conditions shown below, to obtain a compound 53 (4.38 g, 78.2%).

TABLE 8

Reaction Consition Table

| | Fmoc-AAx-OH | AA equivalent | condensing agent | condensing agent equivalent | condensation aid |
|---|---|---|---|---|---|
| 2nd residue | Fmoc-Ser(tBu)-OH | 1.3 | DMT-MM | 1.17 | none |
| 3rd residue | Fmoc-Glu(OtBu)-OH | 1.3 | DMT-MM | 1.17 | none |
| 4th residue | Fmoc-Lys(Boc)-OH | 1.3 | DMT-MM | 1.17 | none |
| 5th residue | Fmoc-Arg(Pbf)-OH | 1.3 | DMT-MM | 1.17 | none |
| 6th residue | Fmoc-Gln(Trt)-OH | 1.3 | DMT-MM | 1.17 | none |
| 7th residue | Fmoc-Gln(Trt)-OH | 1.3 | DMT-MM | 1.17 | none |
| 8th residue | Fmoc-Leu-OH | 1.3 | DMT-MM | 1.17 | none |

| | condensation aid equivalent | base equivalent | reaction condition | scavenger equivalent | HOBt equivalent | DBU equivalent |
|---|---|---|---|---|---|---|
| 2nd residue | none | 1.8 | R.T. for 30 min | 2 | 0 | 7 |
| 3rd residue | none | 1.8 | R.T. for 30 min | 2 | 0 | 10 |
| 4th residue | none | 1.8 | R.T. for 30 min | 2 | 0 | 10 |
| 5th residue | none | 1.8 | R.T. for 30 min | 2 | 0 | 7 |
| 6th residue | none | 1.8 | R.T. for 30 min | 2 | 0 | 10 |
| 7th residue | none | 1.8 | R.T. for 30 min | 2 | 0 | 10 |
| 8th residue | none | 1.8 | R.T. for 30 min | 2 | 0 | 7 |

TABLE 9

Washing Condition Table

| | washing solution (1st) | washing solution (2nd) | poor solvent | suspension-washing solvent |
|---|---|---|---|---|
| 2nd residue | saturated ammonium chloride aqueous solution: water = 1:2 | saturated saline: water = 1:2 | acetonitrile | acetonitrile |
| 3rd residue | saturated ammonium chloride aqueous solution: water = 1:2 | saturated saline: water = 1:2 | acetonitrile | acetonitrile |
| 4th residue | saturated ammonium chloride aqueous solution: water = 1:2 | saturated saline: water = 1:2 | acetonitrile | acetonitrile |
| 5th residue | saturated ammonium chloride aqueous solution: water = 1:2 | saturated saline: water = 1:2 | acetonitrile | acetonitrile |
| 6th residue | saturated ammonium chloride aqueous solution: water = 1:2 | saturated saline: water = 1:2 | acetonitrile | acetonitrile |
| 7th residue | saturated ammonium chloride aqueous solution: water = 1:2 | saturated saline: water = 1:2 | acetonitrile | acetonitrile |
| 8th residue | saturated ammonium chloride aqueous solution: water = 1:2 | saturated saline: water = 1:2 | acetonitrile | acetonitrile |

Synthesis of Compound 54

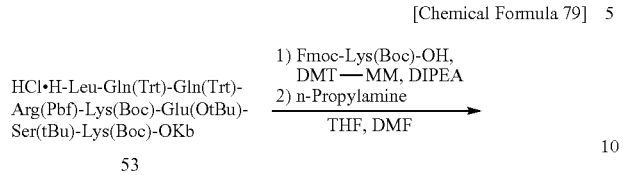

The compound 53 (4.36 g, 1.53 mmol) was operated in the same manner as for the compound 48 using Fmoc-Lys(Boc)-OH (934 mg, 1.99 mmol, 1.3 equiv) and DIPEA (481 μL, 2.76 mmol, 1.8 equiv), to obtain a compound 54 (5.11 g, Quant).

Synthesis of Compound 55 (Fmoc-Lys(Boc)-Leu-Gln(Trt)-Gn(Trt)-Arg(pbf)-Lys(Boc)-Glu(OtBu)-Ser(tBu)-Lys(Boc)-OH)

A Kb protective group general de-protection method was applied on the compound 54 (2.55 g, 0.764 mmol), to obtain a compound 55 (2.26 g, Quant).

(Example 37) Synthesis of Boc-Gly-Ser(tBu)-Ser(n-octanoyl)-Phe-Leu-Ser(tBu)-Pro-Glu(OtBu)-His(Trt)-Gln(Trt)-OH (Compound 61)

Synthesis of Compound 56

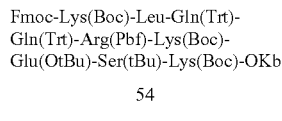

On Kb-OH (2.27 g, 3.0 mmol), Fmoc-Gln(Trt)-OH was used in the same manner as in Example 18, to obtain a compound 56 (4.21 g, Quant).

Synthesis of Compound 57

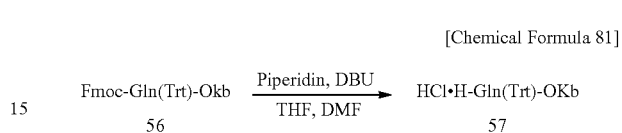

A de-Fmoc general synthesis method was applied on the compound 56 (4.04 g, 2.99 mmol), to obtain a compound 57 (3.62 g, Quant).

Synthesis of Compound 58 (HCl.H-Ser(tBu)-Ser-Phe-Leu-Ser(tBu)-Pro-Glu(OtBu)-His(Trt)-Gln(Trt)-OKb)

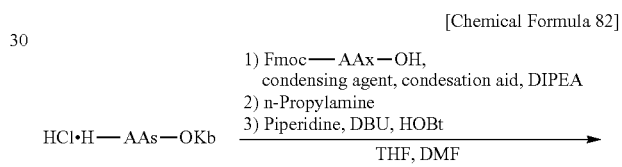

The compound 57 (3.48 g, 2.99 mmol) was processed in the same manner as for synthesis of the compound 20, according to the reaction conditions and washing conditions in the tables below, to obtain a compound 58 (4.60 g, 72.1%).

TABLE 10

Reaction Consition Table

| | Fmoc-AAx-OH | AA equivalent | condensing agent | condensing agent equivalent | condensation aid |
|---|---|---|---|---|---|
| 2nd residue | Fmoc-His(Trt)-OH | 1.3 | DMT-MM | 1.17 | none |
| 3rd residue | Fmoc-Glu(OtBu)-OH | 1.3 | DMT-MM | 1.17 | none |
| 4th residue | Fmoc-Pro-OH | 1.3 | DMT-MM | 1.17 | none |
| 5th residue | Fmoc-Ser(Pbf)-OH | 1.5 | DMT-MM | 1.45 | none |
| 6th residue | Fmoc-Leu-OH | 1.95 | DMT-MM | 1.76 | none |
| 7th residue | Fmoc-Phe-OH | 1.3 | DMT-MM | 1.17 | none |
| 8th residue | Fmoc-Ser-OH | 1.3 | DMT-MM | 1.17 | none |
| 9th residue | Fmoc-Ser(tBu)-OH | 1.3 | DMT-MM | 1.17 | none |

| | condensation aid equivalent | base equivalent | reaction condition | scavenger equivalent | HOBt equivalent | DBU equivalent |
|---|---|---|---|---|---|---|
| 2nd residue | none | 3.6 | R.T. for 30 min | 2 | 1 | 8 |
| 3rd residue | none | 3.6 | R.T. for 30 min | 2 | 0 | 7 |
| 4th residue | none | 3.6 | R.T. for 30 min | 2 | 0 | 7 |

TABLE 10-continued

Reaction Consition Table

| 5th residue | none | 3.6 | R.T. for 30 min | 3 | 0 | 10 |
|---|---|---|---|---|---|---|
| 6th residue | none | 3.6 | R.T. for 30 min | 6 | 0 | 7 |
| 7th residue | none | 3.6 | R.T. for 30 min | 2 | 0 | 10 |
| 8th residue | none | 3.6 | R.T. for 30 min | 2 | 0 | 7 |
| 9th residue | none | 3.6 | R.T. for 30 min | 2 | 0 | 10 |

TABLE 11

Washing Condition Table

| | washing solution (1st) | washing solution (2nd) | poor solvent | suspension-washing solvent |
|---|---|---|---|---|
| 2nd residue | saturated ammonium chloride aqueous solution: water = 1:2 | saturated saline: water = 1:2 | acetonitrile | acetonitrile |
| 3rd residue | saturated ammonium chloride aqueous solution: water = 1:2 | saturated saline: water = 1:2 | acetonitrile | acetonitrile |
| 4th residue | saturated ammonium chloride aqueous solution: water = 1:2 | saturated saline: water = 1:2 | no solidification | no suspension-washing |
| 5th residue | saturated ammonium chloride aqueous solution: water = 1:2 | saturated saline: water = 1:2 | no solidification | no suspension-washing |
| 6th residue | saturated ammonium chloride aqueous solution: water = 1:2 | saturated saline: water = 1:2 | acetonitrile | acetonitrile |
| 7th residue | saturated ammonium chloride aqueous solution: water = 1:2 | saturated saline: water = 1:2 | cold acetonitrile: water = 9:1 | acetonitrile |
| 8th residue | saturated ammonium chloride aqueous solution: water = 1:2 | saturated saline: water = 1:2 | acetonitrile | acetonitrile |
| 9th residue | saturated ammonium chloride aqueous solution: water = 1:2 | saturated saline: water = 1:2 | cold acetonitrile | cold acetonitrile |

Synthesis of Compound 59

[Chemical Formula 83]

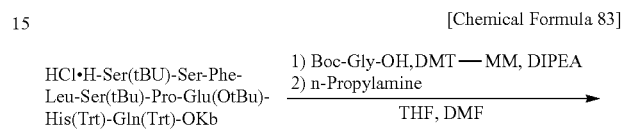

The compound 58 (4.59 g, 1.87 mmol) was operated in the same manner as for the compound 48 using Boc-Gly-OH (425 mg, 2.43 mmol, 1.3 equiv) and DIPEA (1170 μL, 6.72 mmol, 3.6 equiv), to obtain a compound 59 (4.55 g, 94.5%).

Synthesis of Compound 60

[Chemical Formula 84]

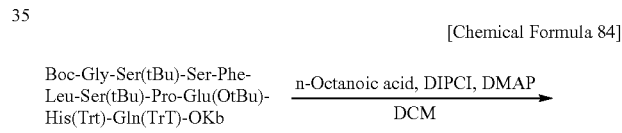

The compound 59 (4.55 g, 1.76 mmol) was dissolved in DCM (35 ml), caprylic acid (628 mg, 3.96 mmol, 2.25 equiv), WSC·HCl (760 mg, 3.96 mmol, 2.2 g equiv) and DMAP (11 mg, 0.088 mmol, 0.05 equiv) were added and the mixture was stirred at room temperature for 30 minutes and at 40° C. for 1 hour. As the amine scavenger, propylamine (1086 μL, 13.2 mmol, 7.5 equiv) was added and the mixture was stirred at room temperature for 30 minutes. A solution of saturated ammonium chloride aqueous solution:water=1:2 of double amount of the reaction solvent was added to the reaction mixture, and the mixture was washed and separated, and the aqueous layer was discarded. Further, a solution of saturated saline:water=1:2 of double amount of the reaction solvent was added, and the mixture was washed and separated, and the aqueous layer was discarded. Further, saturated saline of double amount of the reaction solvent was added, and the mixture was washed and separated, and the aqueous layer was discarded. The resultant organic layer was held under reduced pressure and the solvent was distilled off. To the residue was added acetonitrile, and the deposited precipitate was filtrated, and suspended and washed with acetonitrile, and the resultant solid was dried under reduced pressure, to obtain a compound 60 (4.48 g, 94.1%).

Synthesis of Compound 61 (Boc-Gly-Ser(tBu)-Ser(n-Octanoyl)-Phe-Leu-Ser(tBu)-Pro-Glu(OtBu)-His(Trt)-Gln(Trt)-OH)

A Kb protective group general de-protection method was applied on the compound 60 (4.47 g, 1.65 mmol), to obtain a compound 61 (3.26 g, Quant).

(Example 38) Synthesis of Boc-Gly-Ser(tBu)-Ser(n-Octanoyl)-Phe-Leu-Ser(tBu)-Pro-Glu(OtBu)-His(Trt)-Gln(Trt)-Lys(Boc)-Leu-Gln(Trt)-Gln(Trt)-Arg(Pbf)-Lys(Boc)-Glu(OtBu)-Ser(tBu)-Lys(Boc)-Lys(Boc)-Pro-Pro-Ala-Lys(Boc)-Leu-Gln(Trt)-Pro-Arg(Pbf)-OKb (Compound 63)

Synthesis of compound 62 (HCl.H-Lys(Boc)-Leu-Gln(Trt)-Gln(Trt)-Arg(Pbf)-Lys(Boc)-Glu(OtBu)-Ser(tBu)-Lys(Boc)-Lys(Boc)-Pro-Pro-Ala-Lys(Boc)-Leu-Gln(Trt)-Pro-Arg(Pbf)-OKb)

[Chemical Formula 85]

HCl•H-Lys(Boc)-Pro-Pro-Ala-Lys(Boc)-Leu-Gln(Trt)-Pro-Arg(Pbf)-OKb
50

1) Fmoc-Lys(Boc)-Leu-Gln(Trt)-Gln(Trt)-Arg(Pbf)-Lys(Boc)-Glu(OtBu)-Ser(tBu)-Lys(Boc)-OH,
55
DMT—MM, DIPEA
2) n-Propylamine
3) Piperidine, DBU
⟶
THF, DMF HCl•H-Lys(Boc)-Leu-Gln(Trt)-Gln(Trt)-Arg(Pbf)-Lys(Boc)-Glu(OtBu)-Ser(tBu)-Lys(Boc)-Lys(Boc)-Pro-Pro-Ala-Lys(Boc)-Leu-Gln(Trt)-Pro-Arg(Pbf)-OKb
62

The compound 50 (251 mg, 0.1 mmol) obtained in Example 35 was dissolved in a mixture of THF (9 ml) and DMF (1.0 ml), the compound 61 (443 mg, 0.15 mmol, 1.5 equiv) obtained in Example 36, DMT-MM (40.0 mg, 0.405 mmol, 1.45 equiv) and DIPEA (63 μL, 0.36 mmol, 3.6 equiv) were added and the mixture was stirred at room temperature for 30 minutes. As the amine scavenger, propylamine (25.0 μL, 0.3 mmol, 3 equiv) was added and the mixture was stirred at room temperature for 30 minutes. Piperidine (15 μL, 0.45 mmol, 1.5 equiv) and DBU (150 μL, 3.0 mmol, 10 equiv) were added and the mixture was stirred at room temperature for 10 minutes. Concentrated hydrochloric acid was added until pH of the reaction mixture became around 6. A solution of saturated saline:water=1:2 of double amount of the reaction solvent was added to the reaction mixture, and the mixture was washed and separated, and the aqueous layer was discarded. Further, saturated saline of double amount of the reaction solvent was added, and the mixture was washed and separated, and the aqueous layer was discarded. The resultant organic layer was held under reduced pressure and the solvent was distilled off. To the residue was added cold acetonitrile and the deposited precipitate was filtrated, further, suspended and washed with cold acetonitrile, and the resultant solid was dried under reduced pressure, to obtain a compound 62 (485 mg, Quant).

Synthesis of Compound 63 (Boc-Gly-Ser(tBu)-Ser(n-Octanoyl)-Phe-Leu-Ser(tBu)-Pro-Glu(OtBu)-His(Trt)-Gln(Trt)-Lys(Boc)-Leu-Gln(Trt)-Gln(Trt)-Arg(Pbf)-Lys(Boc)-Glu(OtBu)-Ser(tBu)-Lys(Boc)-Lys(Boc)-Pro-Pro-Ala-Lys(Boc)-Leu-Gln(Trt)-Pro-Arg(Pbf)-OKb)

[Chemical Formula 86]

HCl•H-Lys(Boc)-Leu-Gln(Trt)-Gln(Trt)-Arg(Pbf)-Lys(Boc)-Glu(OtBu)-Ser(tBu)-Lys(Boc)-Lys(Boc)-Pro-Pro-Ala-Lys(Boc)-Leu-Gln(Trt)-Pro-Arg(Pbf)-OKb
62

1) Boc-Gly-Ser(tBu)-Ser(n-Octanoyl)-Phe-Leu-Ser(tBu)-Pro-Glu(OtBu)-His(Trt)-Gln(Trt)-OH,
61
DMT—MM, DIPEA
2) n-Propylamine
⟶
THF, DMF Boc-Gly-Ser(tBu)-Ser(n-Octanoyl)-Phe-Leu-Ser(tBu)-Pro-Glu(OtBu)-His(Trt)-Gln(Trt)-Lys(Boc)-Leu-Gln(Trt)-Gln(Trt)-Arg(Pbf)-Lys(Boc)-Glu(OtBu)-Ser(tBu)-Lys(Boc)-Lys(Boc)-Pro-Pro-Ala-Lys(Boc)-Leu-Gln(Trt)-Pro-Arg(Pbf)-OKb
63

The compound 62 (251 mg, 0.1 mmol) was dissolved in a mixture liquid of THF (2 ml) and DMF (0.2 ml), the compound 61 (295 g, 0.15 mmol, 1.5 equiv) obtained in Example 37, DMT-MM (40.0 mg, 0.405 mmol, 1.45 equiv) and DIPEA (62 μL, 0.36 mmol, 3.6 equiv) were added and the mixture was stirred at room temperature for 30 minutes. As the amine scavenger, propylamine (25.0 μL, 0.3 mmol, 3 equiv) was added and the mixture was stirred at room temperature for 30 minutes. The reaction mixture was held under reduced pressure and the solvent was distilled off. To the residue was added cold acetonitrile and the deposited precipitate was filtrated, further, suspended and washed with cold acetonitrile, and the resultant solid was dried under reduced pressure, to obtain a compound 63 (562 mg, 84.4%).

(Example 39) Synthesis of H-Gly-Ser-Ser(n-Octanoyl)-Phe-Leu-Ser-Pro-Glu-Hi s-Gln-Lys-Leu-Gln-Gln-Arg-Lys-Glu-Ser-Lys-Lys-Pro-Pro-Ala-Lys-Leu-Gln-Pro-Arg-OH (Compound 64)

[Chemical Formula 87]

Boc-Gly-Ser(tBu)-Ser(n-Octanoyl)-Phe-Leu-Ser(tBu)-Pro-Glu(OtBu)-His(Trt)-Gln(Trt)-Lys(Boc)-Leu-Gln(Trt)-Gln(Trt)-Arg(Pbf)-Lys(Boc)-Glu(OtBu)-Ser(tBu)-Lys(Boc)-Lys(Boc)-Pro-Pro-Ala-Lys(Boc)-Leu-Gln(Trt)-Pro-Arg(Pbf)-OKb
63

TFA:TIS:H$_2$O ⟶

-continued

H-Gly-Ser-Ser(n-Octanoyl)-Phe-
Leu-Ser-Pro-Glu-His-Gln-Lys-
Leu-Gln-Gln-Arg-Lys-Glu-Ser-Lys-
Lys-Pro-Pro-Ala-Lys-Leu-Gln-
Pro-Arg-OH

64

The compound 63 (555 mg, 0.083 mmol) obtained in Example 38 was dissolved in 8 ml of a mixture of TFA:TIS:water=95:2.5:2.5, and the mixture was stirred at room temperature for 3 hours. The reaction liquid was filtrated through Celite. The filtration residue was washed with 3 ml of TFA and filtrated. The resultant filtrates were combined together, and concentrated under reduced pressure at room temperature to 4.5 ml. The residue was put into 45 ml of cold isopropyl ether while stirring. The resultant solid was centrifugally separated, and the filtration residue was further suspended and washed with cold isopropyl ether and centrifugally separated, twice. The resultant solid was dried, to obtain a compound 64 (351 mg, Quant, HPLC purity 68.92%). The resultant compound was measured by LC-MS, to observe 1119.3 [M+3H$^+$]/3.

The foregoing merely illustrates objects and subjects of the present invention, and does not limit the accompanying Claims. Without departing from the accompanying Claims, various modifications and alterations to the described embodiments will be apparent to those skilled in the art in view of the teachings herein.

INDUSTRIAL APPLICABILITY

When the peptide synthesis method of the present invention is used, double hit of an amino acid can be prevented in de-protection by deactivating an amino acid active species using a specific scavenger before de-protection of the N-terminal, even if the amino acid active species is not removed from the reaction system. The method of the present invention can solve the problem of an amino acid active species existing in the reaction system in the de-protection reaction, by a simple means, thus, this method is excellent in versatility and useful. Further, a peptide synthesized by the present invention shows less problems of deletion of an amino acid and double hit, and according to the present invention, a peptide of high quality can be synthesized at high yield.

What is claimed is:

1. A peptide synthesis method, comprising:
   (a) condensing an amino acid having an N-terminal protected with fluorenylmethoxycarbonyl (N-Fmoc protected) or an N-Fmoc protected peptide with an amino acid having a C-terminal protected with a carrier which is crystallized according to a change of a composition of a dissolving solvent (C-carrier protected), a C-carrier protected peptide or a C-carrier protected amino acid amide, in the presence of a condensing agent, to obtain an N-Fmoc-C-carrier protected peptide;
   (b) subsequently adding to the reaction system resulting from step (a) at least one amine selected from the group consisting of an alkylamine having 1 to 14 carbon atoms, an aromatic amine having 3 to 14 carbon atoms and hydroxyl amine, wherein the alkylamine or the aromatic amine is a primary or secondary amine;
   (c) thereafter de-protecting the N-terminal; and
   (d) changing a composition of a solvent dissolving the resultant C-carrier protected peptide, to crystallize and separate the C-carrier protected peptide.

2. The peptide synthesis method according to claim 1, wherein said carrier is a compound selected from the group consisting of:

a compound having the following structure:

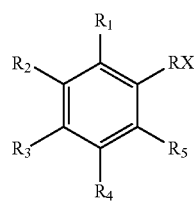

[Chemical Formula 1]

wherein $R_1$ and $R_5$ represent a hydrogen atom, $R_2$, $R_3$ and $R_4$ represent an alkoxyl group having 8 to 30 carbon atoms, and RX is a group represented by the following formula and binding to the C-terminal of a peptide or an amino acid,

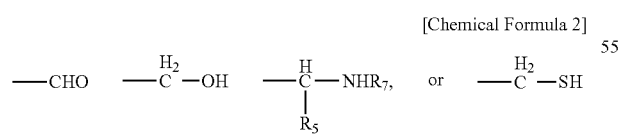

[Chemical Formula 2]

wherein $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group, wherein the above formula is shown in the state before binding to the C-terminal of a peptide or an amino acid, a compound having the following structure:

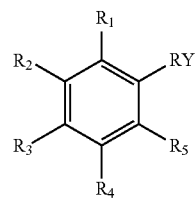

[Chemical Formula 3]

wherein $R_2$, $R_4$ and $R_5$ represent a hydrogen atom, $R_1$ and $R_3$ represent an alkoxyl group having 12 to 30 carbon atoms, and RY is a group represented by the following formula and binding to the C-terminal of a peptide or an amino acid,

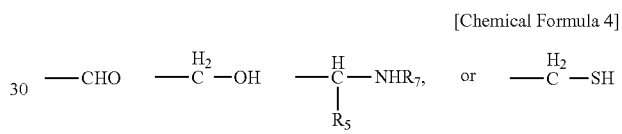

[Chemical Formula 4]

wherein $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group, wherein the above formula is shown in the state before binding to the C-terminal of a peptide or an amino acid, and a compound having the following structure:

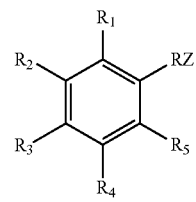

[Chemical Formula 5]

wherein $R_1$, $R_3$ and $R_5$ represent a hydrogen atom, $R_2$ and $R_4$ represent an alkoxyl group having 12 to 30 carbon atoms, and RZ is a group represented by the following formula and binding to the C-terminal of a peptide or an amino acid,

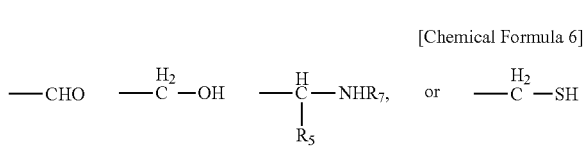

[Chemical Formula 6]

wherein $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group, wherein the above formula is shown in the state before binding to the C-terminal of a peptide or an amino acid.

3. The peptide synthesis method according to claim 1, wherein said carrier is a compound selected from the group consisting of:

[Chemical Formula 7]

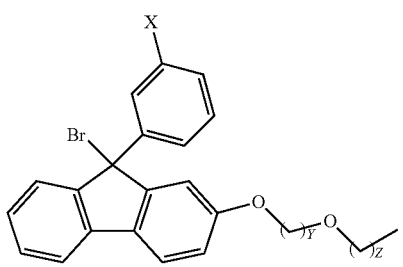

wherein X represents a halogen, Y is an integer of 8 to 12 and Z is an integer of 17 to 29,

[Chemical Formula 8]

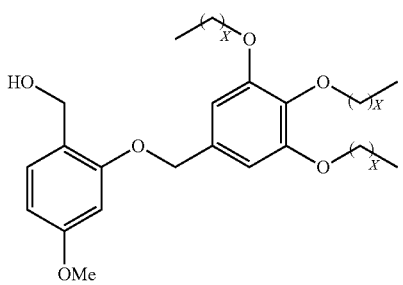

wherein each X independently represents an integer of 7 to 21, and

[Chemical Formula 9]

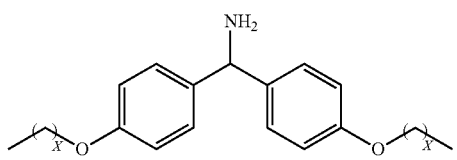

wherein each X independently represents an integer of 11 to 29, wherein the above formulae are shown in the state before binding to the C-terminal of a peptide or an amino acid.

4. The peptide synthesis method according to claim 1, wherein said carrier is a compound selected from the group consisting of:

[Chemical Formula 10]

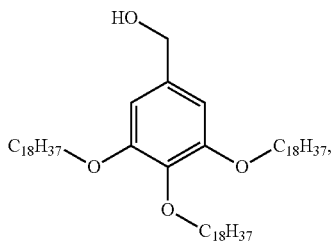

[Chemical Formula 11]

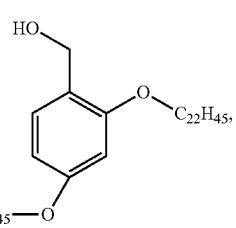

[Chemical Formula 12]

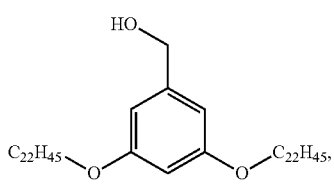

[Chemical Formula 13]

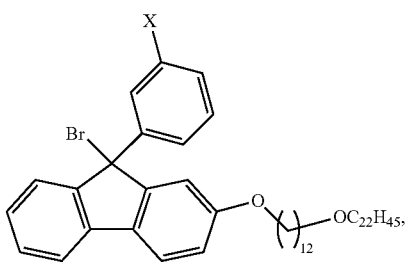

wherein X is F or Cl,

[Chemical Formula 14]

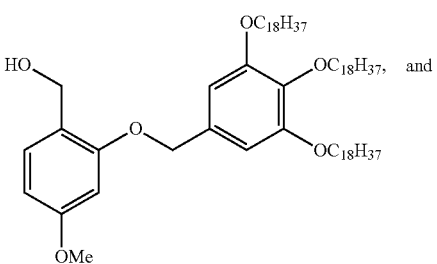

and

[Chemical Formula 15]

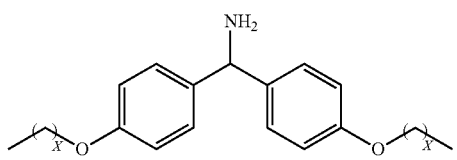

wherein the above formulae are shown in the state before binding to the C-terminal of a peptide or an amino acid.

5. The peptide synthesis method according to claim 1, wherein said amine is an alkylamine having 1 to 10 carbon atoms or hydroxylamine.

6. The peptide synthesis method according to claim 1, wherein said amine is an alkylamine having 3 or 4 carbon atoms.

7. The peptide synthesis method according to claim 1, wherein the amine equivalent in the step (b) is 1 to 30-fold amount with respect to the amino acid equivalent theoretically remaining after the condensation reaction of the step (a).

8. The peptide synthesis method according to claim 1, wherein the composition changing means for changing the composition of the solvent dissolving the resultant C-carrier protected peptide is performed by concentrating the solvent of the solution, then, adding a poor solvent to attain solidification.

9. The peptide synthesis method according to claim 8, wherein said poor solvent is a solvent selected from the group consisting of acetonitrile, aqueous acetonitrile, methanol, aqueous methanol and water.

10. The peptide synthesis method according to claim 1, further comprising repeating the step (a) to the step (d) using the C-carrier protected peptide crystallized and separated in the step (d).

11. The peptide synthesis method according to claim 1, further comprising the following step:
(e) a step of washing the crystal of the C-carrier protected peptide crystallized and separated with an organic solvent.

12. The peptide synthesis method according to claim 1, wherein said steps (a) to (c) are conducted in one pot synthesis.

13. The peptide synthesis method according to claim 2, wherein said amine is an alkylamine having 1 to 10 carbon atoms or hydroxylamine.

14. The peptide synthesis method according to claim 2, wherein said amine is an alkylamine having 3 or 4 carbon atoms.

15. The peptide synthesis method according to claim 2, wherein the amine equivalent in the step b is 1 to 30-fold amount with respect to the amino acid equivalent theoretically remaining after the condensation reaction of the step (a).

16. The peptide synthesis method according to claim 2, wherein the composition changing means for changing the composition of the solvent dissolving the resultant C-carrier protected peptide is performed by concentrating the solvent of the solution, then, adding a poor solvent to attain solidification.

17. The peptide synthesis method according to claim 16, wherein said poor solvent is a solvent selected from the group consisting of acetonitrile, aqueous acetonitrile, methanol, aqueous methanol and water.

18. The peptide synthesis method according to claim 2, further comprising repeating the step (a) to the step (d) using the C-carrier protected peptide crystallized and separated in the step (d).

19. The peptide synthesis method according to claim 2, further comprising the step of:
(e) washing the crystal of the C-carrier protected peptide crystallized and separated with an organic solvent.

20. The peptide synthesis method according to claim 2, wherein said steps (a) to (c) are conducted in one pot synthesis.

21. The peptide synthesis method according to claim 1, wherein, in said step (b), the at least one amine is added to scavenge active esters.

* * * * *

SEQUENCE LISTING

```
<160> NUMBER OF SEQ ID NOS: 13

<210> SEQ ID NO 1
<211> LENGTH: 7
<212> TYPE: PRT
<213> ORGANISM: Artificial Sequence
<220> FEATURE:
<223> OTHER INFORMATION: Sequence prepared using synthetic strategy
      disclosed in the specification

<400> SEQUENCE: 1

Gly Arg Met Asp Arg Ile Gly
1               5

<210> SEQ ID NO 2
<211> LENGTH: 11
<212> TYPE: PRT
<213> ORGANISM: Artificial Sequence
<220> FEATURE:
<223> OTHER INFORMATION: Sequence prepared using synthetic strategy
      disclosed in the specification

<400> SEQUENCE: 2

Gln Ser Gly Leu Gly Cys Asn Ser Phe Arg Tyr
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Sequence prepared using synthetic strategy
      disclosed in the specification
<220> FEATURE:
<221> NAME/KEY: Modification
<222> LOCATION: (3)..(3)
<223> OTHER INFORMATION: Ser at position 3 modified with a Psi Me,Me Pro
      group.

<400> SEQUENCE: 3

Ala Gln Ser Gly Leu Gly Cys Asn Ser Phe Arg Tyr Leu
1               5                   10
```

<210> SEQ ID NO 4
<211> LENGTH: 9
<212> TYPE: PRT
<213> ORGANISM: Artificial Sequence
<220> FEATURE:
<223> OTHER INFORMATION: Sequence prepared using synthetic strategy
      disclosed in the specification

<400> SEQUENCE: 4

Ser Leu Arg Arg Ser Ser Cys Phe Gly
1               5

<210> SEQ ID NO 5
<211> LENGTH: 28
<212> TYPE: PRT
<213> ORGANISM: Artificial Sequence
<220> FEATURE:
<223> OTHER INFORMATION: Sequence prepared using synthetic strategy
      disclosed in the specification
<220> FEATURE:
<221> NAME/KEY: Modification
<222> LOCATION: (19)..(19)
<223> OTHER INFORMATION: Ser at position 19 modified with a PsiMe,Me Pro
      group

<400> SEQUENCE: 5

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 6
<211> LENGTH: 27
<212> TYPE: PRT
<213> ORGANISM: Artificial Sequence
<220> FEATURE:
<223> OTHER INFORMATION: Sequence prepared using synthetic strategy
      disclosed in the specification
<220> FEATURE:
<221> NAME/KEY: DISULFID
<222> LOCATION: (7)..(23)
<223> OTHER INFORMATION: There is a disulfide bond between the Cys at
      positions 7 and 23

<400> SEQUENCE: 6

Ser Leu Arg Arg Ser Ser Ser Phe Gly Gly Arg Met Asp Arg Ile Gly
1               5                   10                  15

Gln Ser Gly Leu Gly Cys Asn Ser Phe Arg Tyr
            20                  25

<210> SEQ ID NO 7
<211> LENGTH: 7
<212> TYPE: PRT
<213> ORGANISM: Artificial Sequence
<220> FEATURE:
<223> OTHER INFORMATION: Sequence prepared using synthetic strategy
      disclosed in the specification

<400> SEQUENCE: 7

Glu Ile Pro Glu Glu Tyr Leu
1               5

<210> SEQ ID NO 8
<211> LENGTH: 7
<212> TYPE: PRT
<213> ORGANISM: Artificial Sequence
<220> FEATURE:
<223> OTHER INFORMATION: Sequence prepared using synthetic strategy -continued

```
<400> SEQUENCE: 8

Gly Gly Asn Gly Asp Phe Glu
1               5

<210> SEQ ID NO 9
<211> LENGTH: 9
<212> TYPE: PRT
<213> ORGANISM: Artificial Sequence
<220> FEATURE:
<223> OTHER INFORMATION: Sequence prepared using synthetic strategy
      disclosed in the specification

<400> SEQUENCE: 9

Lys Pro Pro Ala Lys Leu Gln Pro Arg
1               5

<210> SEQ ID NO 10
<211> LENGTH: 9
<212> TYPE: PRT
<213> ORGANISM: Artificial Sequence
<220> FEATURE:
<223> OTHER INFORMATION: Sequence prepared using synthetic strategy
      disclosed in the specification

<400> SEQUENCE: 10

Lys Leu Gln Gln Arg Lys Glu Ser Lys
1               5

<210> SEQ ID NO 11
<211> LENGTH: 10
<212> TYPE: PRT
<213> ORGANISM: Artificial Sequence
<220> FEATURE:
<223> OTHER INFORMATION: Sequence prepared using synthetic strategy
      disclosed in the specification

<400> SEQUENCE: 11

Gly Ser Ser Phe Leu Ser Pro Glu His Gln
1               5                   10

<210> SEQ ID NO 12
<211> LENGTH: 28
<212> TYPE: PRT
<213> ORGANISM: Artificial Sequence
<220> FEATURE:
<223> OTHER INFORMATION: Sequence prepared using synthetic strategy
      disclosed in the specification

<400> SEQUENCE: 12

Gly Ser Ser Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25

<210> SEQ ID NO 13
<211> LENGTH: 28
<212> TYPE: PRT
<213> ORGANISM: Artificial Sequence
<220> FEATURE:
<223> OTHER INFORMATION: Sequence prepared using synthetic strategy
      disclosed in the specification

<400> SEQUENCE: 13

Gly Ser Ser Phe Leu Ser Pro Glu His Gln Lys Leu Gln Gln Arg Lys
1               5                   10                  15
```

```
Glu Ser Lys Lys Pro Pro Ala Lys Leu Gln Pro Arg
            20                  25
```